United States Patent [19]
Morgan et al.

[11] Patent Number: 5,608,660
[45] Date of Patent: Mar. 4, 1997

[54] AUTOMATED SYSTEM FOR CONTROLLING THE QUALITY OF GEOMETRICALLY REGULAR-SHAPED PRODUCTS DURING THEIR MANUFACTURE

[75] Inventors: Ira L. Morgan; Robert H. Rice; Joseph E. Bolger, all of Austin, Tex.; Donald G. Schindler, Pittsburgh, Pa.

[73] Assignee: Integrated Diagnostic Measurement Corp., Waltham, Mass.

[21] Appl. No.: 323,455

[22] Filed: Oct. 14, 1994

Related U.S. Application Data

[63] Continuation of Ser. No. 531,454, May 31, 1990, Pat. No. 5,379,237.

[51] Int. Cl.$^6$ ................................................ G01B 15/04
[52] U.S. Cl. ...................... 364/562; 364/563; 364/472.06
[58] Field of Search ............................... 378/51, 54–59, 378/62; 72/8, 9, 11, 12, 16, 17; 250/359.1, 360.1, 358.1; 324/240, 243, 242; 364/578, 507, 472, 563, 562, 560, 551.01, 552, 468, 469, 148–150, 152

[56] References Cited

U.S. PATENT DOCUMENTS

| | | | |
|---|---|---|---|
| 3,066,254 | 11/1962 | Price et al. | 250/498.1 |
| 3,108,186 | 10/1963 | Flavell | 378/54 |
| 3,248,916 | 5/1966 | Kenyon et al. | 72/12 |
| 3,496,745 | 2/1970 | Kocks | 72/16 |
| 3,592,031 | 7/1971 | Sutton et al. | 72/8 |
| 3,832,549 | 8/1974 | Mangan et al. | 378/54 |
| 3,841,123 | 10/1974 | Fox et al. | 72/8 |
| 3,851,509 | 12/1974 | Fox | 72/8 |
| 4,098,130 | 7/1978 | Coffey et al. | 73/614 |
| 4,244,025 | 1/1981 | Alshuk | 364/472 |
| 4,415,980 | 11/1983 | Buchanan | 378/58 |
| 4,425,505 | 1/1984 | Jones et al. | 250/359.1 |
| 4,495,635 | 1/1985 | Dobbs | 378/56 |
| 4,535,614 | 8/1985 | Oka | 72/16 |
| 4,558,576 | 12/1985 | Reardon et al. | 72/9 |
| 4,600,998 | 7/1986 | Huet | 364/507 |
| 4,687,343 | 8/1987 | Raffalski | 374/56 |
| 4,725,963 | 2/1988 | Taylor et al. | 364/507 |
| 4,771,622 | 9/1988 | Ginzberg | 72/8 |
| 4,803,639 | 2/1989 | Steele et al. | 364/507 |
| 4,896,278 | 1/1990 | Grove | 364/507 |
| 4,951,222 | 8/1990 | Hoffman et al. | 364/507 |
| 5,303,385 | 4/1994 | Hattori et al. | 364/472 |

FOREIGN PATENT DOCUMENTS

| | | |
|---|---|---|
| 0055781 | 6/1981 | European Pat. Off. . |
| 3327267 | 7/1983 | Germany . |
| 3417633 | 5/1984 | Germany . |
| 54-80263 | 6/1979 | Japan . |
| 56-39112 | 4/1981 | Japan . |
| 59-104209 | 6/1984 | Japan . |
| 60-260807 | 12/1985 | Japan . |
| WO8912281 | 12/1989 | WIPO . |

*Primary Examiner*—Ellis B. Ramirez
*Assistant Examiner*—Hal D. Wachsman
*Attorney, Agent, or Firm*—Jerry M. Keys

[57] ABSTRACT

An apparatus and method for controlling the quality of cylindrical or other geometrically regular-shaped products, such as tube or rounds, through high precision, continuous, real-time three-dimensional analysis of hot or cold products during their manufacture are disclosed. The apparatus includes multiple penetrating radiation sources and detectors. The apparatus is able to continuously and in real time perform a three-dimensional analysis of hot or cold products, detect cross-sectional and longitudinal flaws in the products, determine the processing steps causing the flaw, and modify the production process through feedback and/or feedforward control of the processing equipment. In performing the analysis on hot or cold products, the apparatus can determine the dimensional measurements of the products at other temperatures and take these measurements into consideration while controlling the manufacturing process in order to produce products of consistent dimensional quality.

36 Claims, 19 Drawing Sheets

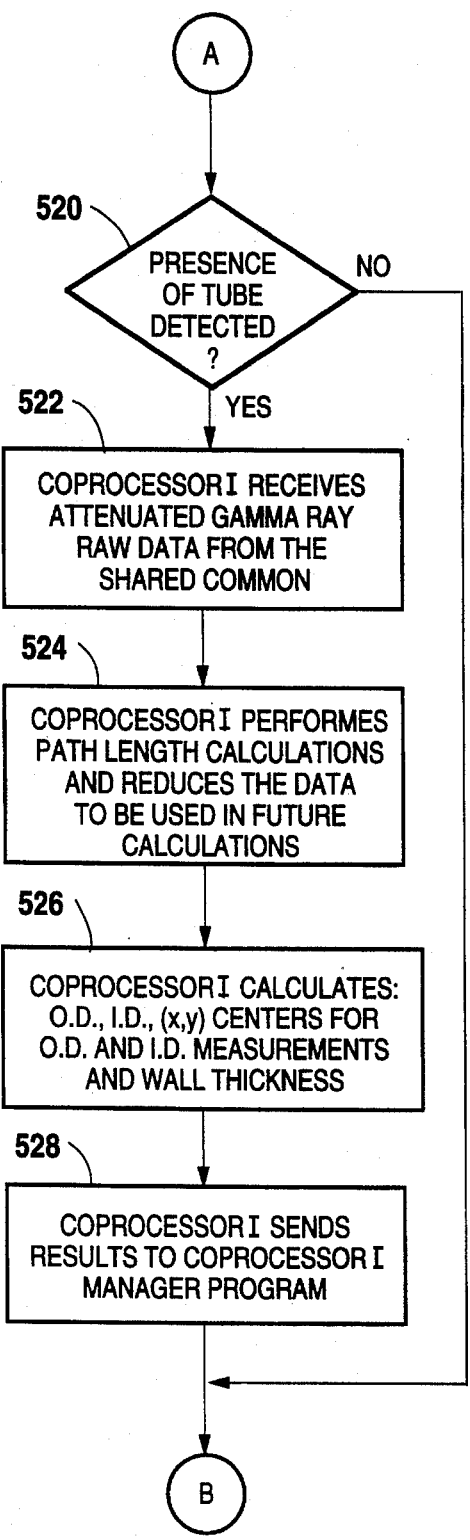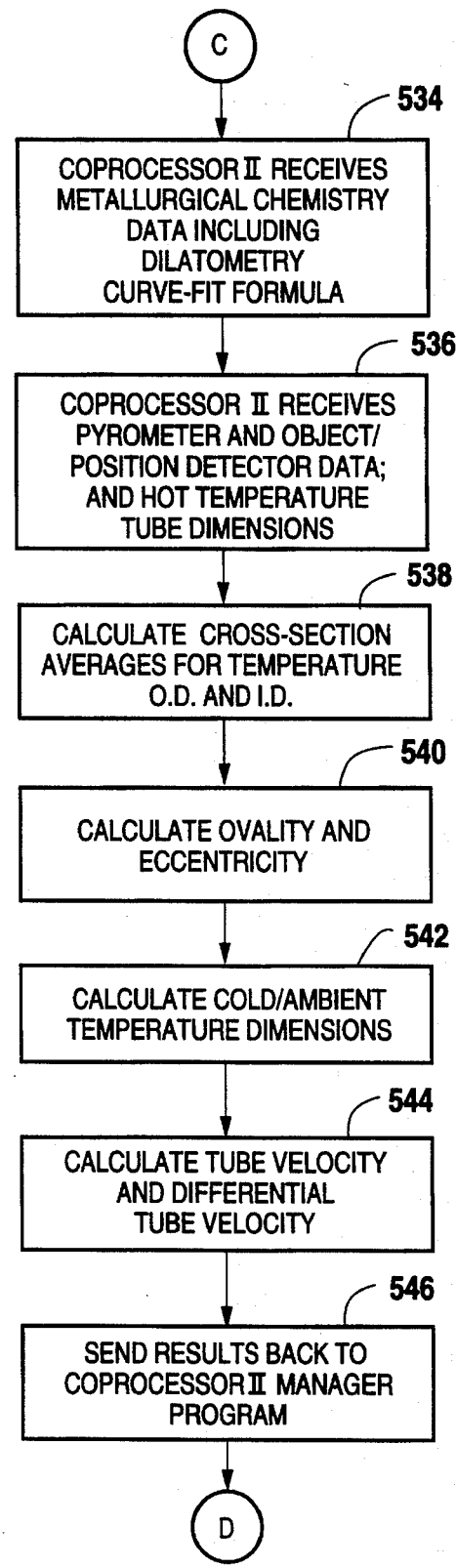
Fig. 8b
Fig. 8c

AUTOMATED SYSTEM FOR CONTROLLING THE QUALITY OF GEOMETRICALLY REGULAR-SHAPED PRODUCTS DURING THEIR MANUFACTURE

RELATED APPLICATION

This patent application is a continuation application from its parent, U.S. patent application Ser. No. 07/531,454 filed on May 31, 1990, for "AN AUTOMATED SYSTEM FOR CONTROLLING THE QUALITY OF REGULARLY-SHAPED PRODUCTS DURING THEIR MANUFACTURE" which issued into U.S. Pat. No. 5,379,237. U.S. patent application Ser. No. 07/531,454 was filed concurrently with U.S. patent application Ser. No. 07/531,322 (now U.S. Pat. No. 5,414,648), in the name of Morgan, et al., entitled "AN APPARATUS AND METHOD FOR NONDESTRUCTIVELY DETERMINING THE DIMENSIONAL CHANGES OF AN OBJECT AS A FUNCTION OF TEMPERATURE", which is directed to a novel apparatus and method for determining dimensional changes of an object as a function of temperature.

BACKGROUND OF THE INVENTION

1. Field of the Invention

The present invention relates generally to a method of, and an apparatus for, automatic quality control in the manufacture of geometrically regular-shaped products, such as tube and rounds, over a wide range of temperatures and, in particular, relates to a method and apparatus that incorporates nondestructive dimensional analysis by means of penetrating radiation and computer models of the product.

2. Description of Prior Art

Technology in many fields has advanced to the level that materials are being pushed to their limits. For this reason, quality control and assurance is becoming increasingly important, not only for production efficiency, but also to prevent failure of a part of a device which could, if undetected, potentially cause loss of property and lives.

In the quality control of any product, it is preferable to test each finite segment of each item of product rather than merely make a random sample. In order to test every product, it is essential that the test be continuous and nondestructive and it is preferable that the test be performed quickly enough to provide real-time control so as not to inhibit the production process.

In the automatic process control of any production process it is also preferable that feedback and feedforward signals for quality control purposes be based on detailed sequential information about every product in the production line, rather than on a random sample of the total product produced. In order to gather data on each unit of product, it is essential that the testing be done so as not to interrupt the production process.

In process control, it is preferable that quality control feedback and feedforward signals be provided as near to real-time as possible. The faster feedback control signals can be delivered to the production process, the less out-of-specification product is produced. In a hot production process this requires that the testing data be collected when the product is at elevated temperatures. The ability to test the product-in-manufacture at elevated temperatures is especially important if control signals are fed forward to additional production processes which can correct the defect while the product remains at elevated temperatures.

In the past, penetrating radiation has been used in several quality control applications. Several of these inventions, as exemplified by U.S. Pat. No. 3,248,916, disclose the use of penetrating X-rays to gauge the thickness of sheet metal. Although U.S. Pat. Nos. 3,841,123 and 3,851,509 teach the use of penetrating X-rays to gauge the final thickness of sheet metal, they both disclose that, even in such simple production processes, the use of X-ray gauges is too slow for automatic process control systems.

One prior art process control system uses X-rays in the production of more complex products. In U.S. Pat. No. 3,496,745, the process control device uses X-rays to measure the average wall thickness of a tube after the last rolling stand and provides feedback. However, this device only provides feedback with respect to one dimensional measurement: the average wall thickness. This testing regimen significantly limits the applicability of the invention to a comprehensive process control system for the production of dense, geometrically-complex products, such as tube or pipe.

U.S. Pat. No. 4,725,963 discloses an apparatus that performs continuous three-dimensional analysis of complex products. However, the patent does not disclose a device that can perform this analysis in real-time on each tube as tubes are produced. Therefore, the system is not capable of being incorporated into a production control process which provides feedback and feedforward information in real-time as the product is being produced.

The invention disclosed in U.S. Pat. No. 4,725,963 is also limited by its inability to consider shrinkage of the product being produced. Although the patent discloses a system that can take measurements of tube at elevated temperatures, it does not correct those measurements to account for shrinkage of the product which accompanies cooling from elevated temperatures.

Further, U.S. Pat. No. 4,725,963 does not include elements necessary for analyzing the measurements generated to identify the types of flaws in the product or their causes and also does not include means for generating, from the dimensional analysis, control signals to modify the manufacturing process for quality control.

U.S. Pat. Nos. 3,496,745 and 4,535,614 disclose systems which suggest adjusting the manufacturing process based on longitudinal flaws. These prior art control systems automatically adjust the roller settings for each product produced to account for the differences between the forces that are imposed on the leading and trailing end of a workpiece. However, the previously disclosed systems assume that the same adjustment is needed for each tube in response to previously developed empirical data. The present invention makes individual adjustments based on the individual data of each workpiece.

In the past, automatic control systems have used means for performing dimensional analysis other than X-rays. U.S. Pat. Nos. 3,841,123 and 3,851,509 illustrate the use of "force gauges on sheet metal." On the other hand, the system in U.S. Pat. No. 4,771,622 uses magnetic detectors on sheet metal. Magnetic detectors are inapplicable to complex shapes, such as tubes or pipes, and are limited to use on materials subject to magnetic detection. Since steel does not possess its magnetic properties at temperatures above the curie temperature, this apparatus cannot be used with a hot steel rolling process. The present invention is applicable to magnetic as well as nonmagnetic materials.

Other systems, as exemplified by U.S. Pat. No. 4,535,614, contemplate the use of a light source and light sensors to measure the shadow of a product. This method is obviously limited to information about the outer surface of an object and is therefore inapplicable to tube and other similarly-shaped products because it cannot detect cavities in such objects.

Historically, multiple process control systems considered the temperature of the workpiece and shrinkage. The invention disclosed in U.S. Pat. Nos. 3,841,123, 3,851,509 and 3,592,031 use temperature data in sheet metal rolling process control systems. However, these systems all made previously determined adjustments to production processes based on the measured temperature. Additionally, all of these systems were simple in that they were concerned with only one dimension of the product: its thickness. The prior systems did not calculate the corrections from the unique metallurgical properties applicable to the specific batch of raw material being used.

SUMMARY OF THE INVENTION

Accordingly, it is an object of the present invention to overcome the limitations of the prior art by providing an apparatus and method for performing continuous three-dimensional analysis of products, such as steel tube and pipe, virtually in real-time. This enables the present invention to be incorporated in a production control process.

Another object of the invention is to provide a method and apparatus to measure the temperature of the product and perform further analysis to correct the dimensional measurements for shrinkage due to cooling.

Another object of the present invention is to perform the additional tasks necessary to generate feedforward and feedback control signals for a process control system.

A further object is to provide a method and apparatus for calibration to increase the accuracy and quality of the dimensional measurements taken by the system.

The present invention provides a new and improved method of and apparatus for obtaining nondestructive real-time three-dimensional measurements of an object with geometrically regular cross-sections during its manufacture. The novel method comprises monitoring the longitudinal position of the object as it moves relative to the scanning apparatus, scanning a cross-section of the object with penetrating radiation, generating signals representative of the attenuation of the radiation as it passes through the cross-section of the object, generating a signal representing the position of the object for each cross-section scanned, and processing the position-indexed cross-sectional scanning signals through the use of a computer model of the object to obtain dimensional measurements of the object's cross-section.

Using the position indexed cross-section dimensional measurements, the present invention also provides a new and improved method of and apparatus for determining characteristics of flaws detected in the object. The novel method comprises: comparing the cross-sectional dimensions of the object to the dimensions of the computer model of an ideal object, thereby generating variance data. The resulting variance data, combined with the cross-section position data, represents flaws and the longitudinal position of the flaw constituting a three dimensional pattern of the flaw.

Using the three dimensional pattern of the flaw, the present invention also provides a new and improved method of and apparatus for automatically identifying the type of flaw and manufacturing steps that caused the flaw by comparing three dimensional pattern characteristics of the flaw with a set of known flaw pattern characteristics and their causes. By matching these patterns, the flaw's type and cause are identified.

The present invention also provides a new and improved method of and apparatus for automatically controlling manufacturing steps to control the quality of the product by measuring the actual dimensions of the object, calculating the variance of actual dimensions from ideal dimensions, identifying the cause of the variance, calculating the adjustment to the processing step required to cure the cause of the flaw and/or the flaw, and transmitting a control signal based on the adjustment calculation to the process equipment which controls the processing step in the manufacturing process responsible for the flaw or to process equipment which can cure the flaw.

The present invention also provides a new and improved method of and apparatus for obtaining real-time, nondestructive ambient temperature dimensions of an object with geometrically regular cross-section by scanning a cross-section of the object with penetrating radiation generating signals representative of the attenuation of the radiation as it passes through the object, processing the signals through the use of a computer model of the object's to obtain dimensional measurements of the object as scanned, measuring the temperature of the object as it is scanned, and finally calculating the ambient temperature dimensions of the object through the use of another computer model which relates the change in dimensions of an object as a function of temperature.

Additionally, the present invention provides a new and improved method of and means for calibrating an apparatus that scans objects with penetrating radiation in order to generate information concerning the dimensions of the object. The novel method comprises of a plate with multiple pin locations, a set of plates of varying thickness, and a computer algorithm which processes the data collected with the calibration plates to generate calibration factors to be used in the normal operation of the apparatus.

BRIEF DESCRIPTION OF THE DRAWINGS

FIGS. 8a–h are illustrative data flow diagram of signals originating at the source/detector as they are processed by the apparatus shown in FIG. 2.

FIGS. 9a–h are illustrations of flaw characteristics which can be detected by the apparatus shown in FIG. 2a.

DESCRIPTION OF THE PREFERRED EMBODIMENT

Figure 1:
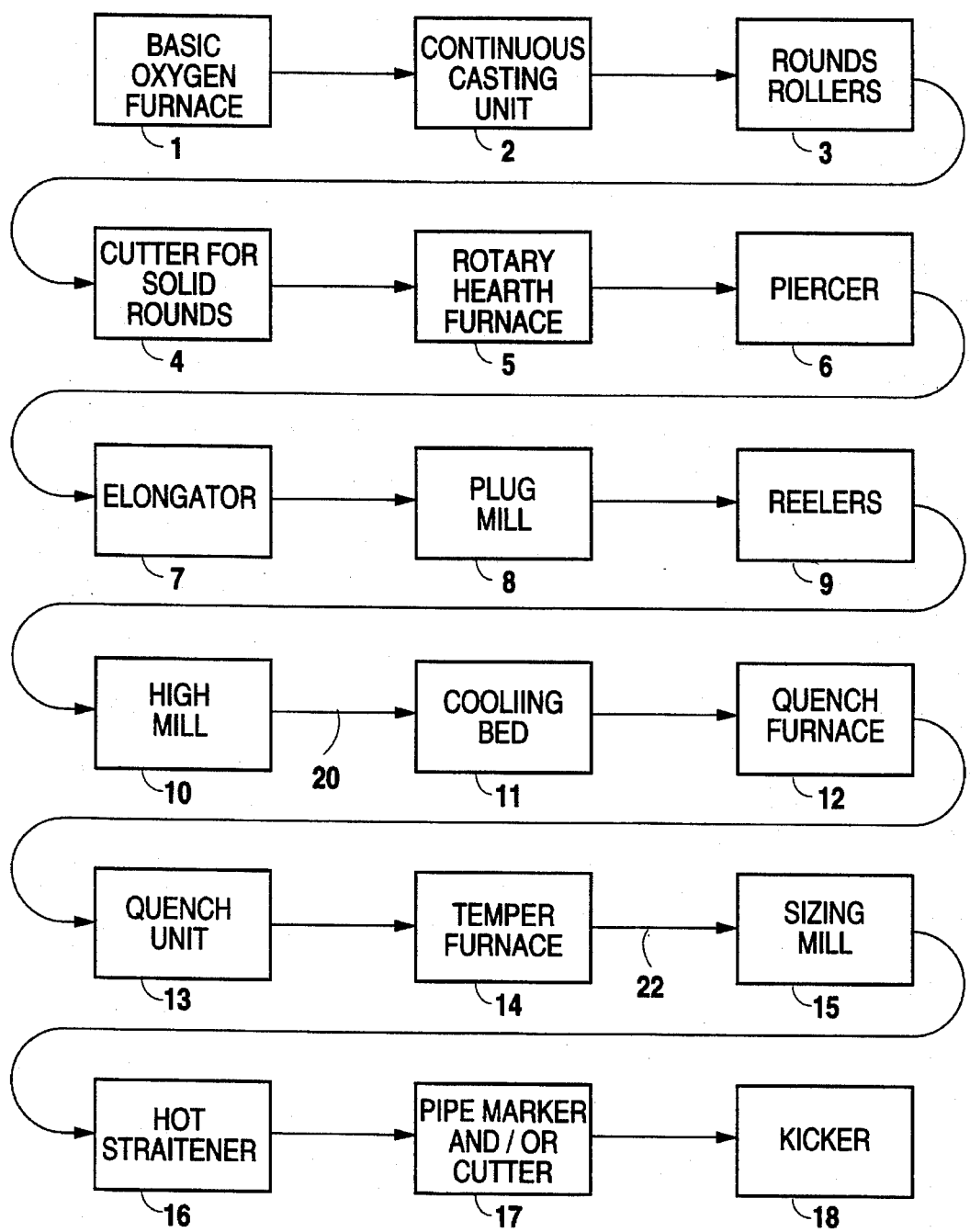
FIG. 1 is a simplified diagrammatic illustration of production flow in a typical seamless tube mill in which the present invention may be employed.

FIG. 1 is a diagrammatic illustration of a typical seamless tube mill into which the invention disclosed below may be integrated. The basic oxygen furnace 1 produces steel from iron ore. The continuous casting unit 2 casts a long continuous rough billet, which is shaped into rounds-by rollers 3. The solid rounds are then cut by a cutter 4 and placed in a rotary hearth furnace 5. After the rounds are brought up to temperature by the rotary hearth furnace 5, the piercer 6 makes a hole down the center of the round which now resembles a tube. The elongator 7, plug mill 8 and reelers 9 elongate the tube, smooth out the inner surface of the tube, and make the wall thickness uniform through the length of the tube. The tube is then run through a high mill 10, which produces the final inner diameter and wall dimensions, and then is allowed to slowly cool on the cooling bed 11. The tube is then reheated in the quench furnace 12 and quenched in the quench unit 13. A temper furnace 14 again reheats the tube and finishing touches are performed by the finishing mill 15 and the hot straightener 16. Finally, both ends of the tube are cropped by the tube cutter 17 and the resulting tube is kicked off the line by kicker 18 and stored for shipment.

Historically, calibration equipment was located at the end of the production line after the pipe was completed and had significantly cooled. The tests using this equipment were often destructive, requiring that a sample be cut for testing and then scrapped.

Waste also results from cutting excessive lengths from the ends of the tube. Every tube produced must have both ends cropped because both ends are irregular and out of specification due to inherent characteristics of the manufacturing process. Historically, due to lack of information of where the tube dimensions fell into specification, the cut was made liberally resulting in significant waste.

Additionally, a great deal of waste results from the delay from manufacture to testing. In order to correct a manufacturing process, dimensional changes or other flaws in the product must first be detected. In order to detect the flaw, the product must be tested. Meanwhile, during the delay, the uncorrected manufacturing process continues to produce tube that would also have to be scrapped for being out of specification. Decreasing this delay decreases the amount of waste.

Figure 2A:
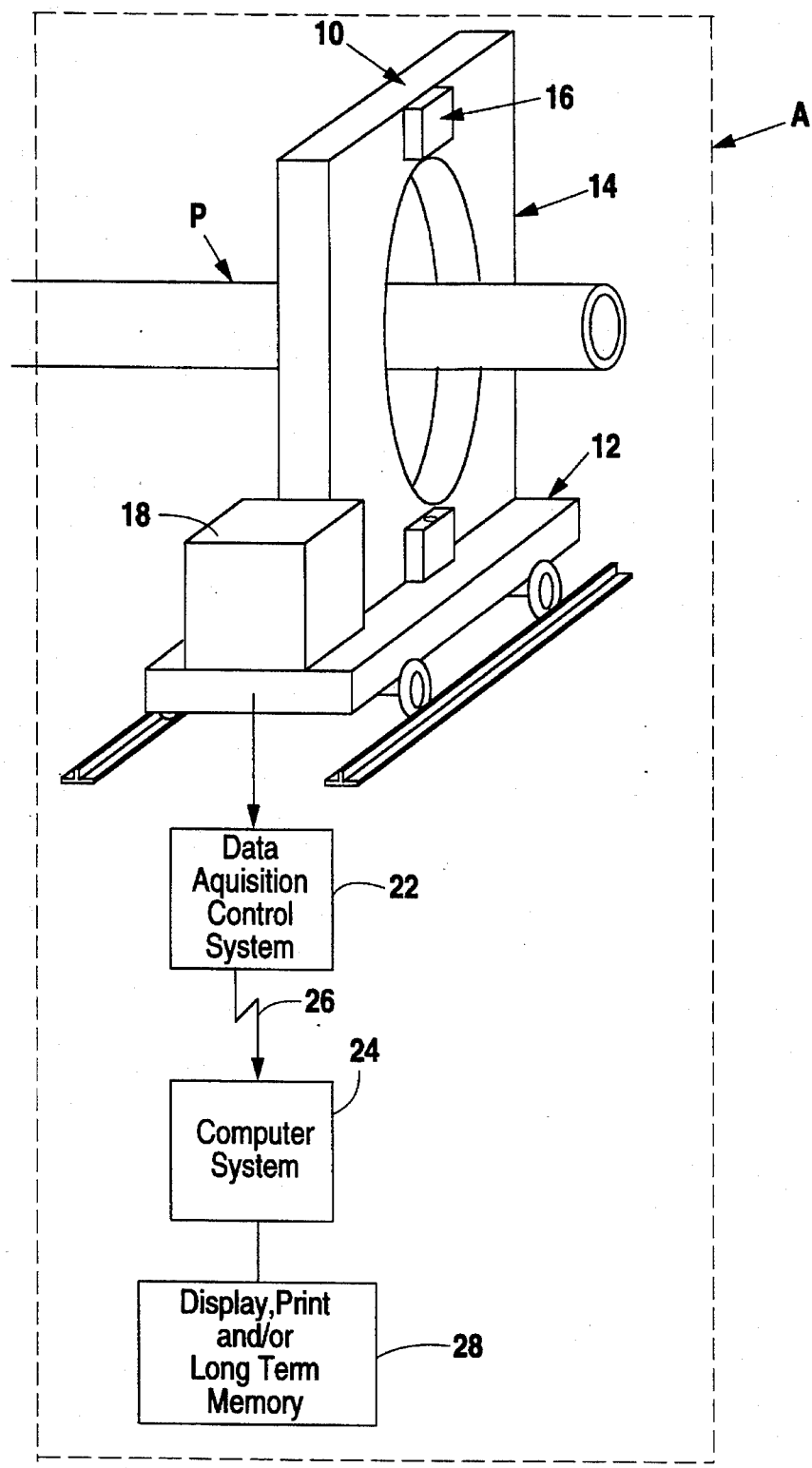
FIG. 2a is an illustrative schematic diagram of the apparatus of the present invention in a production line positioned between the finishing rollers and the paint marking device.

In contrast to existing calibration equipment, the preferred location 20 of the apparatus A, shown in FIG. 2a of the present invention, is between the high mill 10 and the cooling bed 11. At this location, the apparatus A receives the tube P directly after it has been shaped by the piercer 6, elongator 7, plug mill 8, reeler 9, and first high mill 10. This allows the apparatus A to provide feedback to all of the prior production steps to prevent defects in future production with less delay and also provide important feedforward information to down-line production process equipment concerning the tube P, which was actually scanned so that certain defects identified can be cured.

However, the apparatus A is not limited to placement at the preferred location 20 in a seamless tube mill. It can be placed in other positions along the production line. For example, the invention can be located at location 22 between the temper furnace 14 and the finishing sizing mill 15. At this location, the tubular product P, entering the apparatus A, has been shaped, sized, quenched and tempered and feedforward information can be sent to a finishing mill 15 for corrections and also to the hot straightener 16 and paint marker or tube cutter 17. The apparatus A may be modified to fit into a different location in the production line shown in FIG. 1 to identify and provide process control information concerning defects in the product.

The apparatus A disclosed is not limited to the seamless pipe mill production process; it can be used in other processes. For example, with only a few minor changes, the apparatus A can readily be used, for example, in extrusion, continuous casting, electro-resistant and machining production processes and processes which make welded pipes, rods or bars. The apparatus and method disclosed is for production processes of cylindrical products; however, when modified with appropriate modeling algorithms, the method is useful in the production process of any geometrically regular-shaped object. Hereinafter, for purposes of facilitating the descriptions, the term "tube P or product P" shall mean the billet, round tube or finished pipe P, depending on the context of the description.

In FIG. 2a, the apparatus A is placed in a tube production line between the high mill rollers 10 and a paint marker 17, for illustrative purposes. The tube P travels from left to right in the figure. Object detectors 30 monitor the progress of the tube P as it travels down the production line. These object detectors 30 are used to determine the velocity and position of the tube P at various stages in the production process. The object detectors 30 are necessary for the quality control of production steps, such as cutting or marking the cut off distance from both ends of the tube and for determining the product length. The exact location of the tube P in the tube cutter 17 must be available to the apparatus A so that the tube P can be cut at the correct location.

A source/detector apparatus 32, described in greater detail below, is positioned in the path of the tube P in the production line on a rail cart 34. The rail cart's path is defined by two rails 36 which pass perpendicular and underneath the tube's path. Mounted to the housing 38 of the source/detector apparatus 32 are at least one, and preferably two or more, pyrometers 40 which measure the temperature of the tube P close to the source/detector apparatus 32. A suitable pyrometer is a non-contact temperature transducer capable of measuring objects between 1200 and 2000 degrees Fahrenheit by detecting the wavelength of the infrared radiation. The field of view of the pyrometer should be large enough to get a good average temperature of the object. Small spot sizes may show discrete differences in the measured temperature. A one inch diameter spot size should be adequate. The response time should be adjustable in the 50 ms to 1s time range and is set according to the speed at which the object is traveling.

A module 42 is also mounted on the rail cart 34. The module 42 includes an electronics assembly for conditioning the signals from the source/detector apparatus 32, which will be described in more detail below. Electronic signals generated by the module 42 are collected by a data acquisition and control system 44. The data acquisition and control system 44 further processes the collected signals and sends the resulting information to a suitable computer system 46, via a high-speed communications link 48. The module 42 may also be incorporated within the protective housing 38.

The high-speed communications link 48 enables the computer system 46, and associated peripherals discussed below, to be located remotely from the harsh electromagnetic noise, vibrations, dirt and elevated temperatures found within the typical environment of a production mill shown in FIG. 1. A preferred communications link 48 is a fiber optic system which would provide high-speed data transmission with minimal noise interference.

The computer system 46, described in greater detail below, processes the signals from the data acquisition control system 44 to continuously generate dimensional analysis of the tube P and determine which processing equipment needs adjustment.

The computer system 46 then transmits control signals to an automatic process control interface by another high-speed communications link. Preferably, the computer system 46 is connected to two automatic process control interfaces: one for feedback control 50, via link 52, and the other for feedforward control 54, via link 55. The use of two automatic process control interfaces 50 and 54 is preferred because of the particular production process and the location in which the source/detector scanner apparatus 32 is located in FIG. 1. In another production process, only one automatic process control interface may be necessary.

The automatic process control interfaces 50 and 54 condition the control information and send feedback and feedforward signals to adjusting motors marking systems, cutters, etc., via links 56 and 58, respectively, to modify one or more process components of the production process in FIG. 1 to account for the defects measured and detected by the apparatus A. In cases where a defect cannot be automatically corrected, the computer system 46 generates a message which informs the operator of the defect and its likely cause.

Feedforward information is also sent from the feedforward control interface 54, via link 58a, to a component in the production process in FIG. 1, such as to the paint markers or tube cutters 17, which mark or cut off the ends of the tube P where the tube P is out of specification.

The computer system 46 is also connected to several peripherals 62, via link 61, to graphically display, print and store data in permanent memory devices.

THE SAFETY AND ENVIRONMENTAL CONTROL SYSTEM

The environment of a production mill, such as a seamless steel tube mill, can be harsh and hostile to much of the equipment used with the invention. Such environments are typically polluted with dirt, dust, moisture, high temperatures, vibration, noise, and electromagnetic fields.

Figure 2B:
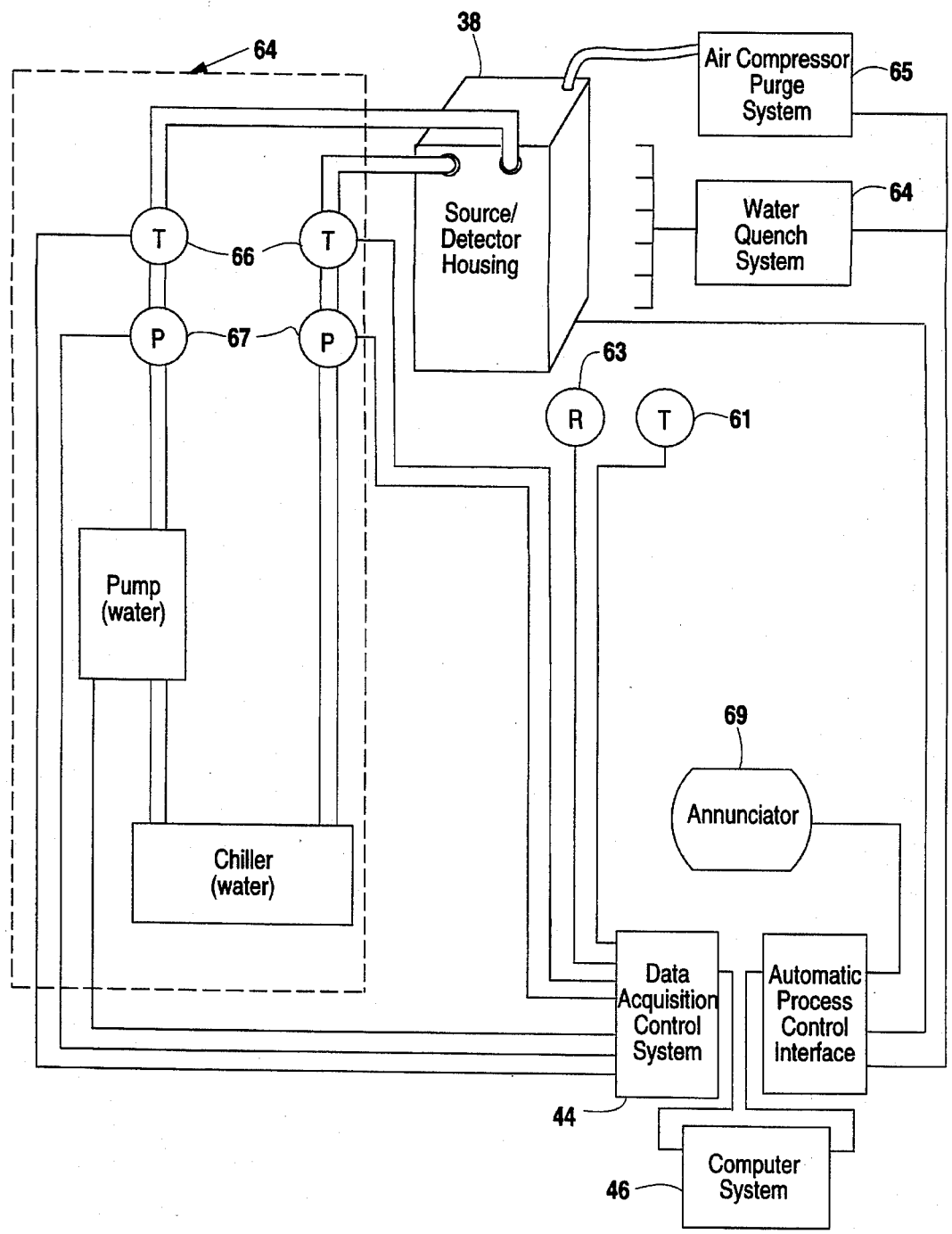
FIG. 2b is an illustrative schematic diagram of the environmental and safety control system of the apparatus.

The apparatus A (FIGS. 2a and 2b) of the present invention incorporates several methods of protecting components of the apparatus. The computer system 46 and its peripherals 52, 128 and 129 are protected from the harsh environment by being located elsewhere, thus removing them from the harsh environment of the mill. This is accomplished by incorporating a high-speed fiber optic communication link that allows the computer system and its peripherals to be removed from the mill, without significantly affecting the time delay. An added benefit of the fiber optic communication link 48 is its virtual immunity to the high level of electromagnetic noise interference, which is commonly found in a manufacturing environment.

Nevertheless, several components of the source/detector apparatus 32 and the signal conditioning module 42 cannot be removed from the production environment. The data acquisition control system 44 and the automatic process control interfaces 50 and 54 remain in the production environment, but are placed in air-tight protective enclosures. These enclosures are designed to protect the system 44 and interfaces 50 and 54 from dust, debris, temperature fluctuations, electromagnetic noise, vibrations and other hostile conditions. The source/detector apparatus 32 is similarly enclosed in a protective housing 38. The interior of these housings is environmentally controlled through a positive pressure air conditioning system. Slight positive pressure is used to prevent mill dirt from entering the enclosures. This positive pressure is supplied through an air compressor 65.

The protective housing 38, in which the source/detector apparatus 32 is housed, has additional environmental and safety features. These features are required because of heat radiating from the hot tube P that passes through the source/detector apparatus 32 and heat generated as a result of the electronics power dissipation within the housings 38 and 42. (See FIGS. 2a and 2b.) The housing 38 includes: inside temperature and radiation monitors (not shown) and outside monitors 61 and 63 of the housing 38, a water quench system 64, which quenches the tube P if the production line stops, and the temperature inside the housing 38 rises above a safe level, an air compressor system 65 to convectionally cool the housing 38 from the outside between tubes, a chiller system 68 with internal water temperature sensors 66, and pressure sensors 67 which circulates chilled water inside the housing to protect the source/detector apparatus 32 from the radiant heat from the hot tube. If unsafe conditions are discovered, the computer will sound an alarm 69 through an annunciator and shut down the source/detector apparatus 32. The safety and environmental control system is monitored and controlled by the computer system 46, as described below in the description of the main computer software.

THE SOURCE/DETECTOR APPARATUS

Figure 3A:
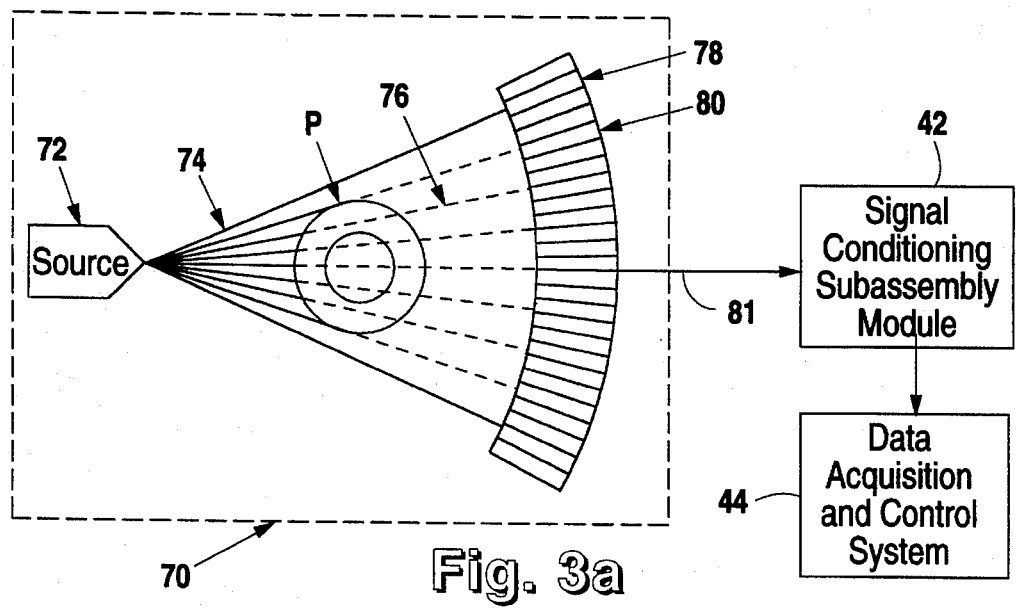
FIG. 3a is a simplified diagrammatic representation of a source/detector which forms a part of the multiple source/detector apparatus of the present invention.

FIG. 3A illustrates one source and detector array pairing 70. The source/detector apparatus 32 is composed of at least two of such source/detector pairs. In the preferred embodiment of the invention, there are three pairings 70 in the source/detector apparatus 32.

Figure 3B:
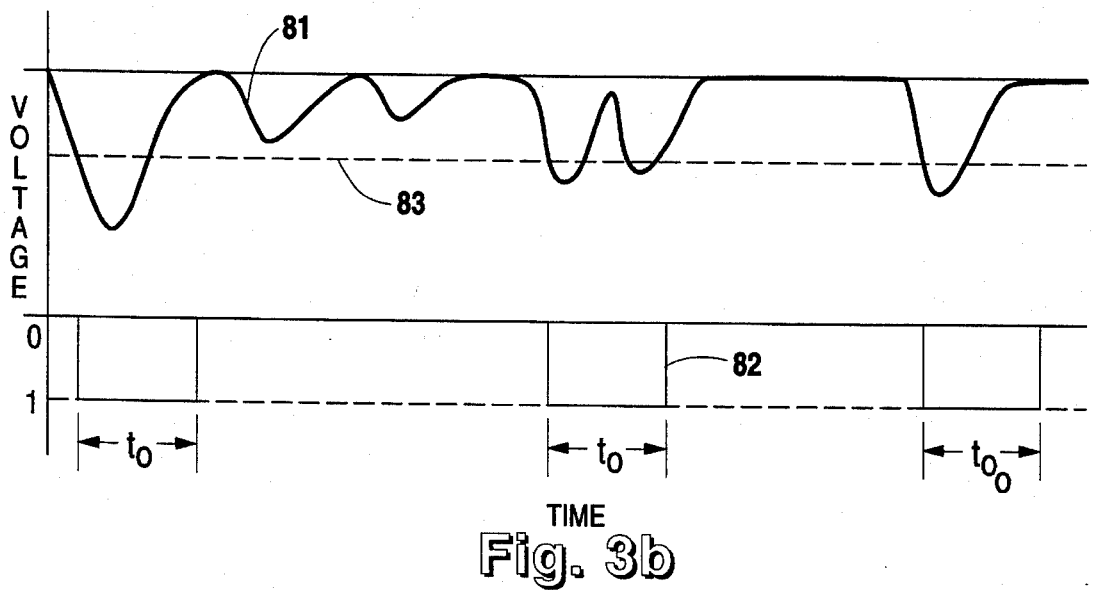
FIG. 3b is a schematic of the signal conditioning subsystem of the apparatus of FIG. 2.
Figure 4:
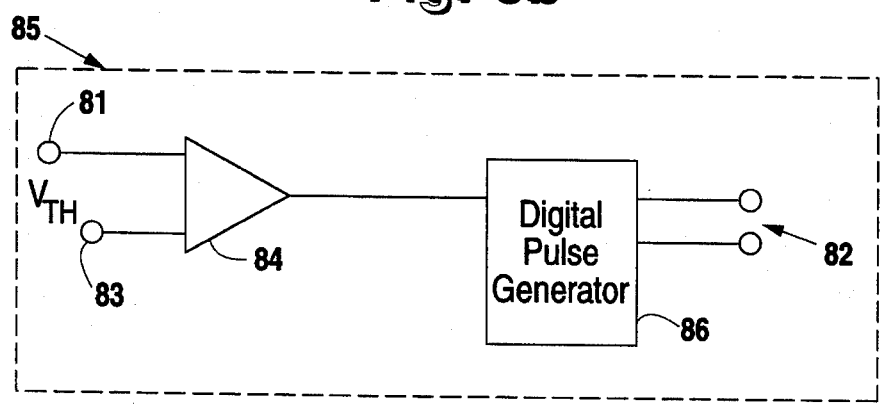
FIG. 4 is a graphic illustration of the signal generated by a detector of FIG. 3a, and the converted signal generated by the signal conditioning subsystem of FIG. 3b in response to the receipt of a detector signal.

The source 72 emits a beam 74 of gamma or X-ray radiation which passes through the entire cross-section of tube P. The attenuated gamma ray or X-ray beam 76 on the opposite side of the tube P is detected by a detector array 78 which is composed of many tightly packed detectors 80. Each of the detectors 80 generate fast analog voltage signals 81, illustrated in FIG. 3b, in response to the gamma rays or X-rays detected by a detector 80. These analog signals 81 are then transmitted to multiple channels 85 of the signal conditioning module 42. One channel is shown in FIG. 4. Each channel 85 of the module 42 includes a conventional ultra-fast comparator 84 which has one input connected to the link 81 from a detector. The second input is connected to an adjustable voltage source $V_{TH}$ which provides the threshold voltage 83 to the comparator. The comparator generates a trigger pulse which is then transmitted to a digital pulse generator 86. The generator 86 generates a digital pulse or conditioned signal in response to a trigger pulse at its input, but only if the trigger pulse occurs after the fixed dead time period $t_o$, as shown in FIG. 3b, prior to collection by the data acquisition control system 44. Except as described herein, suitable sources 72 and detector arrays 78 are described in U.S. Pat. No. 4,725,963.

Since the analog signals 81 have varying amplitudes and occur randomly due to the randomly emitted photon events from a source 72, each channel 85 of module 42 is designed to generate a digital pulse or conditioned signal 82, only when the analog signal from a detector 80 has an amplitude greater than a threshold level 83. Once triggered, the channel 85 of module 42 cannot generate another conditioned signal 82 for a fixed time period $t_o$ called "dead time." The fixed dead time period allows for an accurate correction of the number of pulses counted.

Each detector 80 has slightly different recovery times in which it can recover from sensing one pulse and sensing a following pulse. This is due to the random nature of the incoming signal 81 pulse height and width. During a detector's recovery time, additional pulses may enter the detector 80. This piling up of pulses must be corrected for. Since each detector 80 has a different recovery time, the corrections can be complicated. To simplify the correction, the circuitry sets a fixed dead time, uniform for each detector, which is greater than the largest recovery time. By using a fixed dead time, the proportion of time for which the detectors do not respond to incoming radiation is known. Knowing this proportion, the measured radiation count can be corrected to account for the total actual radiation which entered the detector. For example, if the measured radiation count was 900 and the total dead time accounted for 10% of the total time, the actual radiation count is calculated to be 1000. Using a uniform fixed dead time for all detectors allows the use of one formula for all the detectors 80; therefore, it is not necessary and is impractical to determine the response time of each individual detector.

DATA ACQUISITION

Figure 5:
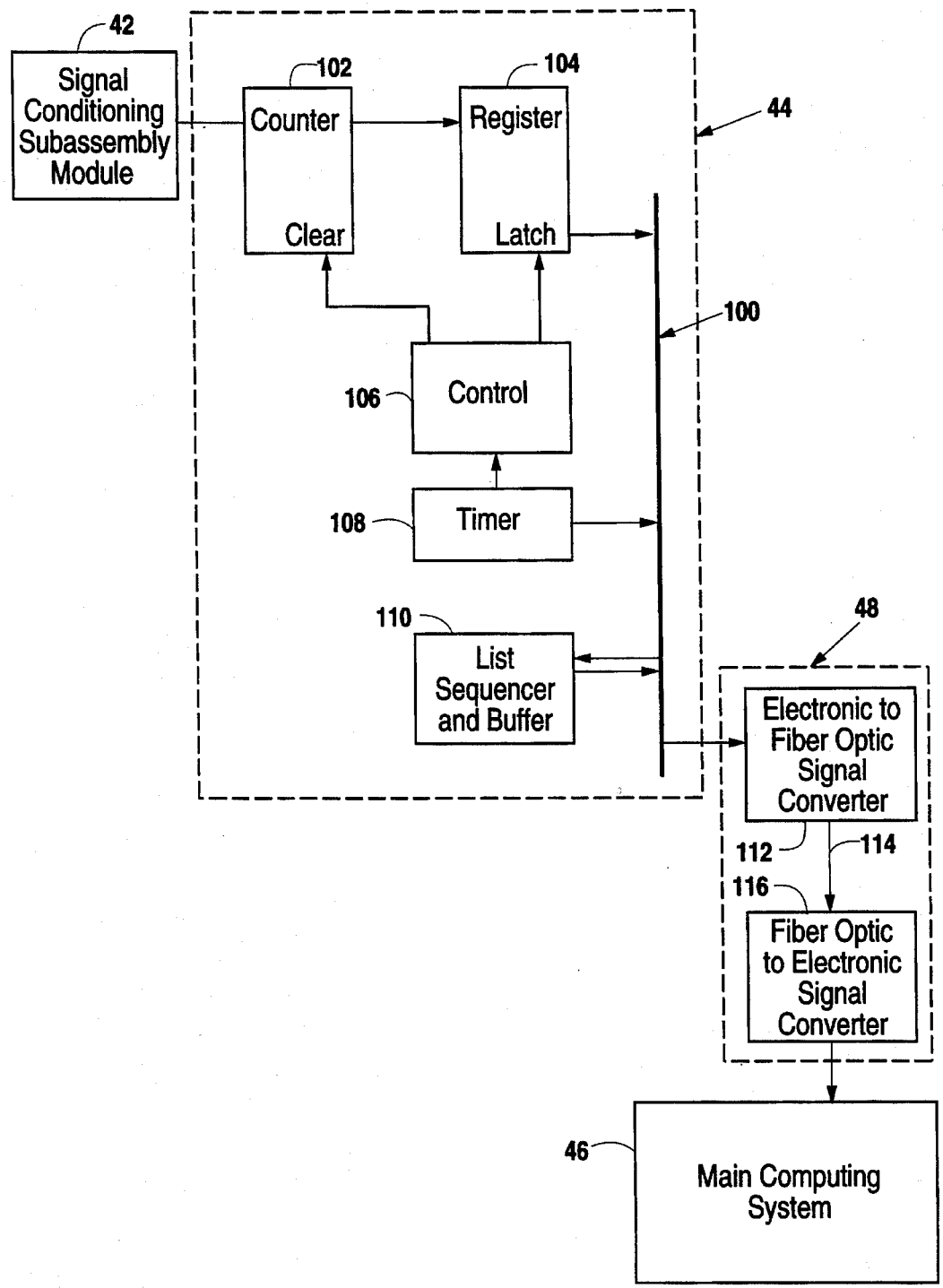
FIG. 5 is a schematic diagram of the data collection control subsystem of the apparatus of FIG. 2.

FIG. 5 provides for a more detailed description of how one channel 85 of data is collected and transmitted from the signal conditioning subassembly 42 to the computer system 46. The digital signals coming from each detector conditioning channel 82 is transmitted to a conventional counter 102, which continuously counts the number of times the signals exceed a predetermined threshold value. A data register 104 periodically latches onto the count in the counter 102 at a predetermined sampling rate and transmits the count to the data acquisition subsystem data bus 100. Immediately after the register 104 latches onto the count, the counter 102 is cleared and continues counting from zero. The latching of the register 104 and clearing of the counter 102 is effectuated by a conventional controller 106. The controller 106 has, at its disposal, a timer 108 which transmits time information to the controller 106 and the data bus 100. A suitable list sequencer and buffer 110 collects data sent from the data register 104 and blocks the data in compact format before sending the data to the computer system 46, via a suitable high-speed communication link 48 capable of transmitting 32 bit words at a rate up to 5 megabytes per second. A suitable high-speed communications link 48 is a fiber optic connection with 100 micrometer optical fiber core with attenuation of 5 dB/Km or less. An electronic-to-fiber optic signal converter 112 converts the digital signal into light pulses transmitted along a fiber optic cable 114. On the other end of the cable 114, the optical signals are reconverted into a digital signal by a fiber optic to electronic signal converter 116 which transmits the digital electronic signal to the computer system 46.

COMPUTER PROCESSING

Figure 6:
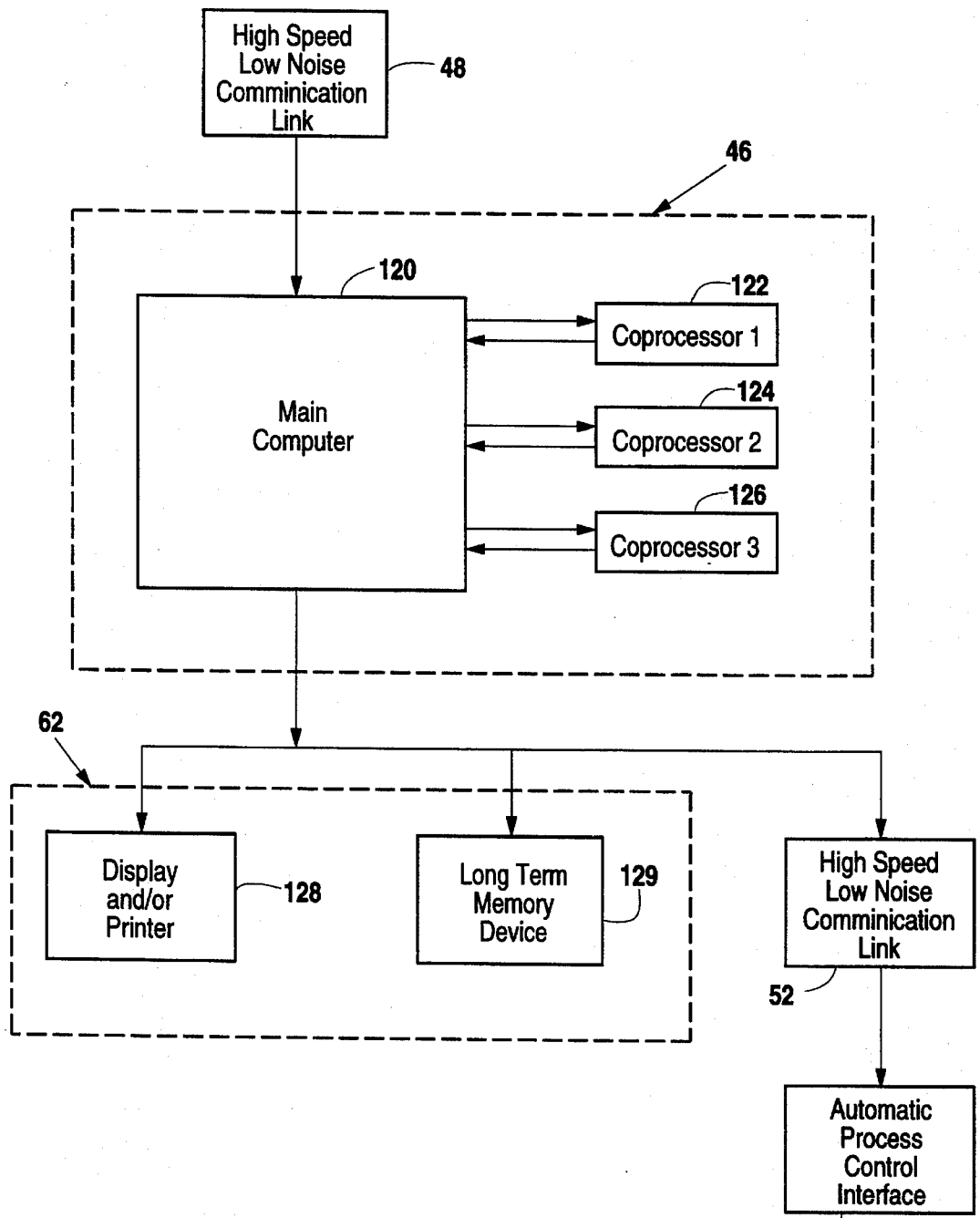
FIG. 6 is a schematic diagram of the computer system hardware and peripherals forming part of the apparatus of FIG. 2.

The hardware structure of the computer system 46 is illustrated in FIG. 6. The computer system 46 obtains data from the data acquisition and control system 44 through a high-speed, low noise communication link 48. Preferably, the computer system 46 is comprised of a main computer 120, with three peripheral coprocessors 122, 124, 126. A suitable main computer is a Digital Equipment Corporation (DEC), MicroVax II with at least 4 megabytes of main memory and a processing rate of approximately 0.9 MIPS. Array processors with processing data rates of 20 million floating point instructions per second are suitable coprocessors.

The computer 120 is programmed to act as the central data processing hub which assigns specific data processing tasks to the three coprocessors and performs the balance of the data processing itself. The computer 120 also serves as the operator's link to the other components of the apparatus A.

The general purpose of the three coprocessors is to increase the effective processing data rate of the computer system 46 through parallel processing. The coprocessors are each assigned specific data processing tasks which can run in parallel.

For example, coprocessor 122 computes the path length of the radiation through the tube and performs analytical data reduction, described hereinafter, to determine the data points that will be used by other programs to reach a final result. At the same time, coprocessor 124 takes in the dimensional measurements (OD, ID, wall thickness, eccentricity, ovality and length) of hot tube and metallurgical chemistry and dilatometry data in order to calculate the cold dimensions of the product after cooling. While coprocessors 122 and 124 perform their calculations, coprocessor 126 calculates the dimensional variance between the measured dimensions and the desired dimensions. From these variances, coprocessor III 126 identifies flaws and generates signals which either correct the flaw or inform the operator of the flaw and its probable cause. The data processing tasks performed by coprocessors 122, 124 and 126 will be disclosed in greater detail below.

Alternatively, the DEC MicroVax and three coprocessors could be replaced by any other computer system capable of interfacing to the required peripherals and data acquisition electronics and which has a total processing rate equal to or exceeding the MicroVax and its coprocessors.

The computer system 46 is also connected to numerous peripherals 128 and 129, which can display or print information and also store or archive data in long-term memory devices.

MAIN COMPUTER SOFTWARE

Figure 7A:
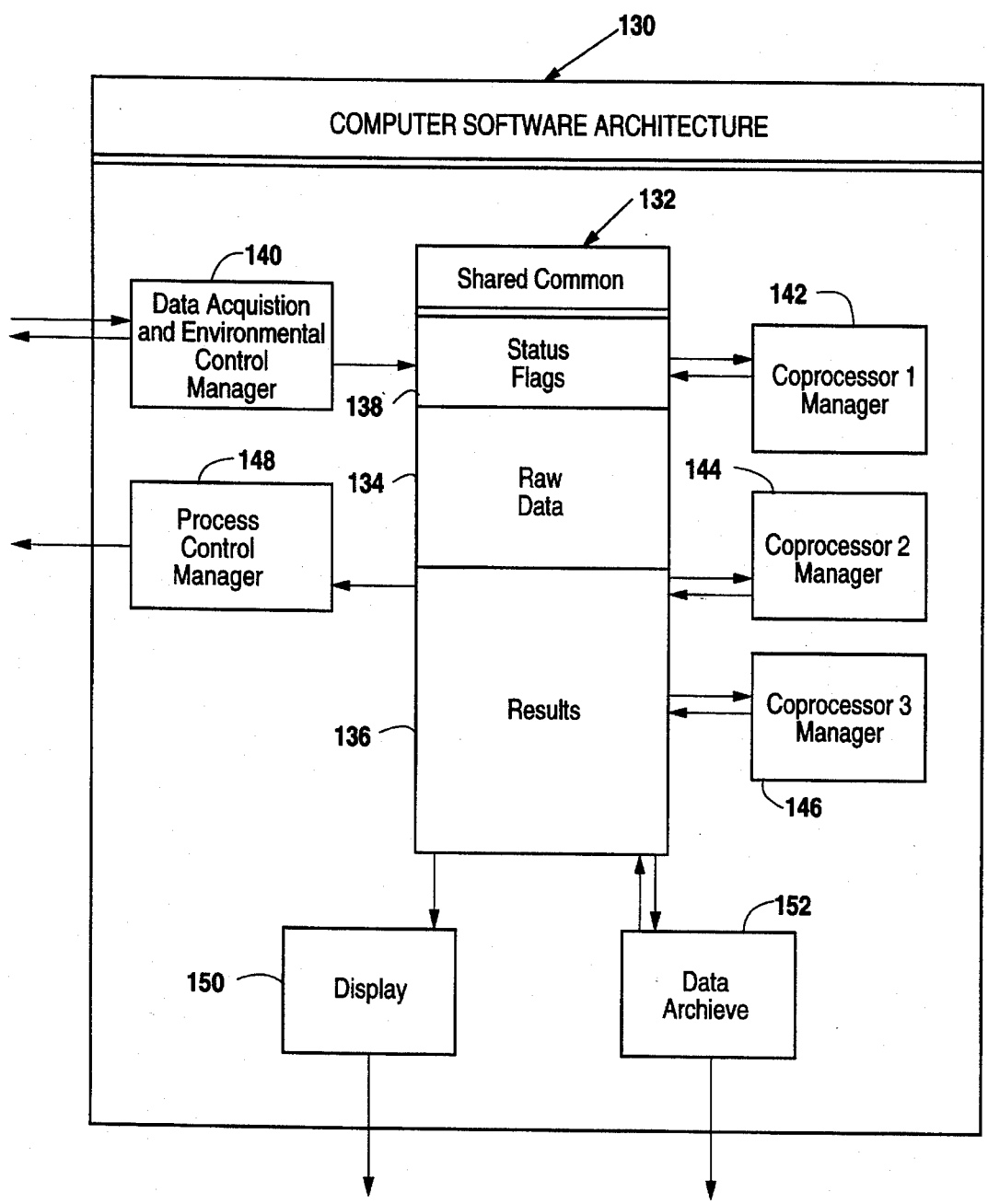
FIG. 7a is a diagrammatic illustration of the software architecture of the computer system shown in FIG. 6.

The application software architecture 130 of the main computer 120 is illustrated in FIG. 7a. The software architecture 130 is centered around shared common memory 132, which is a partitioned section of the main memory of the computer which makes data available to the various programs described herein, which need the information to complete their tasks. The shared common memory 132 is itself divided into several partitions. One partition 134 holds raw or unprocessed data received from the data acquisition control system 44, which has not yet been processed by the computer system 46; a second partition 136 holds processed data or results from various stages of computation; and a third partition 138 holds status flags, which signal the programs described herein, to begin collecting data from partition (s) 134 and/or 136. After the resident programs have finished collecting data from the shared common memory 132 and performed the processing tasks assigned to the programs, the results are copied into partition 136 and signal flags in partition 138 are changed, signaling other programs, described below, that the data in partition(s) 134 and/or 136 needed to perform their tasks is available.

The preferred embodiment of the invention utilizes seven application programs, described below, that run on the main computer 120.

One of these seven programs is the data acquisition and environmental control manager 140. The environmental control functions of this program 140 are disclosed in greater detail, supra. The data acquisition functions of this program 140 involve collecting data which has been sent to the computer system 46, from the data acquisition control system 44, via a high-speed communication link 48, and depositing the data in the shared common 132.

The computer also contains three coprocessor manager programs 142, 144, and 146 for supervising coprocessors 122, 124, and 126, respectively. The main function of programs 142, 144, and 146 is to send data from partitions 134 and 136 to coprocessor 122, 124, or 126, and to bring the coprocessors' results back to be stored in partition 136. The manager program 142 for coprocessor 122 takes raw data from partition 134 of the shared common memory 132, sends it to coprocessor 122 which performs its processing task, receives the results, performs additional computations, described below, and finally copies the results into partition 136 of the shared common memory 132.

The coprocessor manager program 144 takes the results placed in partition 136 by the coprocessor manager program 122 and sends it to coprocessor 124, which performs its processing task, receives the results, performs additional computations, and copies the results into partition 136 in the shared common memory 132.

The coprocessor manager program 146 takes the results placed in partition 136 by the coprocessor manager 144 and sends them to coprocessor 126, which performs its processing tasks, receives the results, performs additional computations, and copies the results in partition 136 of the shared common memory 132. The processing tasks for each coprocessor 122, 124, and 126 and coprocessor manager programs 142, 144, and 146 are disclosed in greater detail below.

Another manager program in the main computer 120 is called the process control manager 148. This program 148 coordinates sending process control information to the automatic process control interface 50.

A display program 150 in the main computer 120 provides for a user interface with the apparatus A. This program 150 is disclosed in more detail hereinafter.

The data archive program 152 electronically stores, in a permanent memory device 62, selected data and results generated by the computer system 46. However, in the preferred embodiment, the data archive program 152 also performs additional functions. For example, the data archive program performs several calculations, described below, relevant to the entire length of a piece of tube P before electronically archiving data in its memory device 62.

These seven programs do not run in any particular order; however, they typically are prioritized. For example, operating safety is of primary importance; therefore, the program which monitors and controls the apparatus' environmental control equipment is given priority. Or, by way of another example, if measuring an entire piece of tube P is more important than displaying the information in real time, the programs necessary to measuring the tube P take priority over the display program. If quality control is more important than process control, which is usually true, programs necessary for detecting flaws will take priority over the programs necessary for determining the cause of a flaw.

Since the preferred embodiment of this invention was intended for use in a tube production mill (FIG. 1), there is an interval of time available between pieces of tube P for performing calculations. The computer system 46 takes advantage of this time period by performing certain calculations, described hereinafter, in the data archive program 152. However, in an alternative embodiment, the apparatus does not require time intervals to function continuously in real time. A fourth coprocessor, (not shown in the drawings), can be used to free the main computer 120 of the time required to perform the calculations performed in the data archive program 152.

Preferably, if a second tube P enters the source/detector 32 while the data archive program 152 is running, the main computer 120 will abandon running the data archive program 152 and will begin running the data acquisition and environmental control manager 140. This abandonment may take place if the operator is more interested in quality control and detection of flaws for the entire piece of tube P, rather than immediate process control. Therefore, the data acquisition program 140 received higher priority than the data archive program 152.

DATA ACQUISITION AND ENVIRONMENTAL CONTROL MANAGER

Considering the seven programs described above in more detail, the primary function of the data acquisition and environmental control manager 140 is to receive data from the data acquisition control system 44. The program 140 begins by initializing all data acquisition counters 102 in the data acquisition control system 44. The program may shift into a standby mode and wait for the data acquisition list sequencers 110 to collect a predetermined set of raw data, for example, five sets of raw data. Once the plurality of sets of raw data has been collected, program 140 accepts the raw data and places it in partition 134 of the shared common memory 132 to make it available to the other programs previously described. The transfer of such sets of raw data at one time is not necessary, but is preferably done in order to reduce the amount of overhead time associated with transferring information into the main computer 120.

In addition to acquiring data from the source/detector apparatus 32, program 140 also collects data from pyrometers 40. The electronic signal from the pyrometer 40 is used to calculate the temperature of the tube P for each cross-section scanned. The calculation is performed in coprocessor II 124 as described below. Temperature data is acquired in a manner that allows for continuous temperature readings along the length of the tube P. This temperature data is crucial to the dilatometry calculations also performed by coprocessor II 124. Both the source/detector data and the pyrometer data are collected through the use of a fast monitoring routine in program 140, since this data must be collected at a high sampling rate. For safety reasons, readings from radiation monitors 63 are also collected using the same fast monitoring routine to assure that radiation is kept within safe limits. If radiation readings are abnormally high, this program 140 will sound an alarm 69 and, if the radiation is abnormally extreme, will force the radiation sources 72 to shut down.

In addition to the fast monitoring data acquisition function, the data acquisition and environmental control manager 140 performs several slow monitoring functions. The slow monitoring activities include acquisition of data concerning air temperature not shown and pressure not shown inside the detector housing 38, cooling water, temperature 66, pressure 67, and cycling of mill air purge system 65. The program sounds an alarm 69 when air temperature and pressure go outside a specific range, indicating a system failure. If the temperature or pressure conditions become too dangerous, this program 140 will shut down the entire system and activate the water quench system 64.

COPROCESSOR I MANAGER

The purpose of the coprocessor I manager 142 is to calculate outside diameter, inside diameter, and (x,y) centers of the two diameters. The program runs cyclically—initializing when the data acquisition manager 140 trips a status flag in partition 138 of the shared common memory 132 indicating that a data set 32 from the data acquisition and environmental control manager is stored in the shared common memory 132. However, before performing these calculations, a number of other calculations must be performed. One of these calculations is to determine the length of material in the paths between the source 72 and each detector 80. This is possible because the presence of a solid object, such as tube P in the path of the gamma rays 74, attenuates the gamma ray signal 76 received by the detector 80. The greater the length of material the gamma rays 74 must travel through, the greater the attenuation of gamma rays.

The computational burden of calculating these path lengths is passed to a coprocessor 122 that is peripheral to the main computer 120. The coprocessor I program 142 periodically sends one set of scaler data to coprocessor I 122, allowing the main computer 120 to perform other tasks, while coprocessor I 122 is working on calculating path lengths. To calculate the path lengths for a set of scaler data, the coprocessor 122 must have access to two additional sets of scaler data: the background count rate and the air count rate. The background count rate is obtained while the radiation source 72 is closed; the air count rate is obtained while the radiation source 72 is open, with no solid objects in the gamma ray beam 74.

Before using the air count rate and the tube attenuated count rate in any calculations, these count rates must be corrected for the interval of time that the signal conditioning subassembly 42 is inhibited by the detection of a gamma ray pulse. During this time, gamma rays 74 are entering the detectors 80, but are not being counted. This short interval of time, described earlier as "dead time," is accounted for by the following formulas:

$$A_i' = A_i/[1 - A_i(T_1/T_2)]$$

$$P_i' = P_i/[1 - P_i(T_1/T_2)]$$

where "i" ranges from 1 to the maximum number of detectors 80, "$A_i$" represents the air count, "$P_i$" represents the tube attenuated count, "$T_1$" represents the time that the channel is inhibited after a pulse is detected; "$T_2$" represents the data acquisition time, and "$A_i'$" and "$P_i'$" represent the dead time corrected count rates.

"$T_1/T_2$" is typically approximately $1.5 \times 10^{-6}$, and the quantities $A_i(T_1/T_2)$ and $P_i(T_1/T_2)$ are much less than 1 in practical applications. It is normally not necessary to correct the dead time for the background count rate because the count rate is slow enough that the correction is insignificant.

After dead time corrections have been made to the air count and tube attenuated count, the background count, "$B_i$", is subtracted from the tube attenuated count and the air count:

$$A_i'' = A_i' - B_i$$

$$P_i'' = P_i' - B_i$$

where "$A_i'$" represents the air count after being corrected for dead time, and "$P_i'$" represents the tube attenuated count after being corrected for dead time.

After the dead time and background count corrections have been completed, it is also necessary to correct for radiation that has deviated from its path and undesirably entered into a detector out of line of its original path. This radiation is called "scattered radiation." Scattered radiation is a by-product of the interaction of the gamma rays with the atoms in the tube P. The attenuation is caused by gamma rays hitting atoms in the wall of tube P and being absorbed or scattered. Unfortunately, some of the scattered radiation is picked up by detectors 80, not originally in the line of the radiation 74 as it leaves the source. The detector 80 readings are therefore corrected to account for the proportion of the count caused by scattered radiation rather than direct emissions. However, before completing this task, the air count and pipe count data are normalized as if each had a constant flux of radiation. This step is necessary because each detector 80 has uncontrollable differences in radiation detection efficiencies which must be normalized when considering the count rate corrections in a detector based on the count rate in neighboring detectors. The normalized air count rates, $A_i'''$, and pipe count rates, $P_i'''$, are:

$$A_i''' = C/D_i^2$$

$$P_i''' = P_i''[A_i'''/A_i'']$$

where "C" is a totally arbitrary constant, "$D_i$" is the source to detector distance, "$A_i''$" and "$P_i''$" are the dead time corrected, background subtracted air and pipe count rates, respectively. The "$D_i^2$" term corrects the constant radiation flux rate for differences in distance between the sources and each detector.

After the tube attenuated count rate has been normalized, corrections can be made for radiation scattering caused by the detectors 80 themselves, rather than the tube P. This type of scattering is commonly called "interdetector secondary scattering." Corrections for interdetector secondary scattering are accounted for by:

$$P_i'''' = P_i''' - \Sigma_j [N_j(P_{i+j}''' + P_{i+j}''')]$$

where "J" and the "$N_j$" are determined empirically from calibration measurements.

A final correction to the count rate is attributed to radiation scattering from the pipe itself and other supporting construction materials. This correction is proportional to the count rate and does not consider variations from detector to detector. The fully corrected count rates are then:

$$P_i''''' = P_i'''' - BA_i'''$$

where "B" is determined empirically from calibration measurements.

Path lengths are calculated using "$P_i'''''$" and "$A_i'''$" through the formula:

$$L_i = F \ln (A_i'''/P_i''''')$$

where the value of "F" is related to the X-ray absorptivity, "$\mu$" and density, "p" by $$F = (1/\mu p)$$

The X-ray absorptivity is dependent upon the X-ray energy and pipe chemical composition. The pipe material density, p, depends upon the chemical composition and temperature.

Finally, the path lengths are corrected to account for the nonlinearity of path lengths from one detector 80 to the next. This is done with the following quadratic formula:

$$L_i' = X_i + (Y_i)(L_i) + (Z_i)(L_i)^2$$

where "$L_i'$" is the corrected length, "$L_i$" is the uncorrected length and "$X_1$", "$Y_i$" and "$Z_i$" are factors which were determined by the calibration measurements.

In addition to calculating path lengths, coprocessor 122 also performs a data reduction task to determine which data points will be used to calculate the outside diameter and inside diameter of the tube P and then corrects the data points for an aperture size as described below.

The data is reduced through the use of the following analysis. The three detector arrays see a shadow of the tube P of varying intensity. This shadow is commonly called the tube profile. There is a sharp difference where the shadow begins on the detector array 78. Continuing along the length of the detector array 78, the shadow becomes progressively darker. The shadow becomes distinctly lighter again where the inner diameter of the tube P begins. From the point where the inside diameter begins until the center of the tube P, the shadow becomes progressively lighter. After the center of the tube, the shadow becomes darker until it become distinctly darker where the inner diameter ends. At the point the inner diameter ends, the shadow becomes progressively lighter until the shadow abruptly ends. These distinct changes in the shadow are used to determine the inside and outside diameters of the tube P.

However, prior to performing these calculations, the data points must be corrected for aperture size by indexing a table containing values appropriate for the specified size of tube P that is being produced. In this way, the number of and distance between the path length data points which will be used in further calculations is determined.

Since the edges of the inside diameter may not correspond to the index set by the outside diameter indexing determination above, the index to be used to calculate the inside diameter is offset from the starting outside diameter index by the following formula:

$$\text{Index} = \text{INTEGER } (C_1 + (\text{wall})(C_2))$$

where "$C_1$" and "$C_2$" are constants.

Figure 7B:
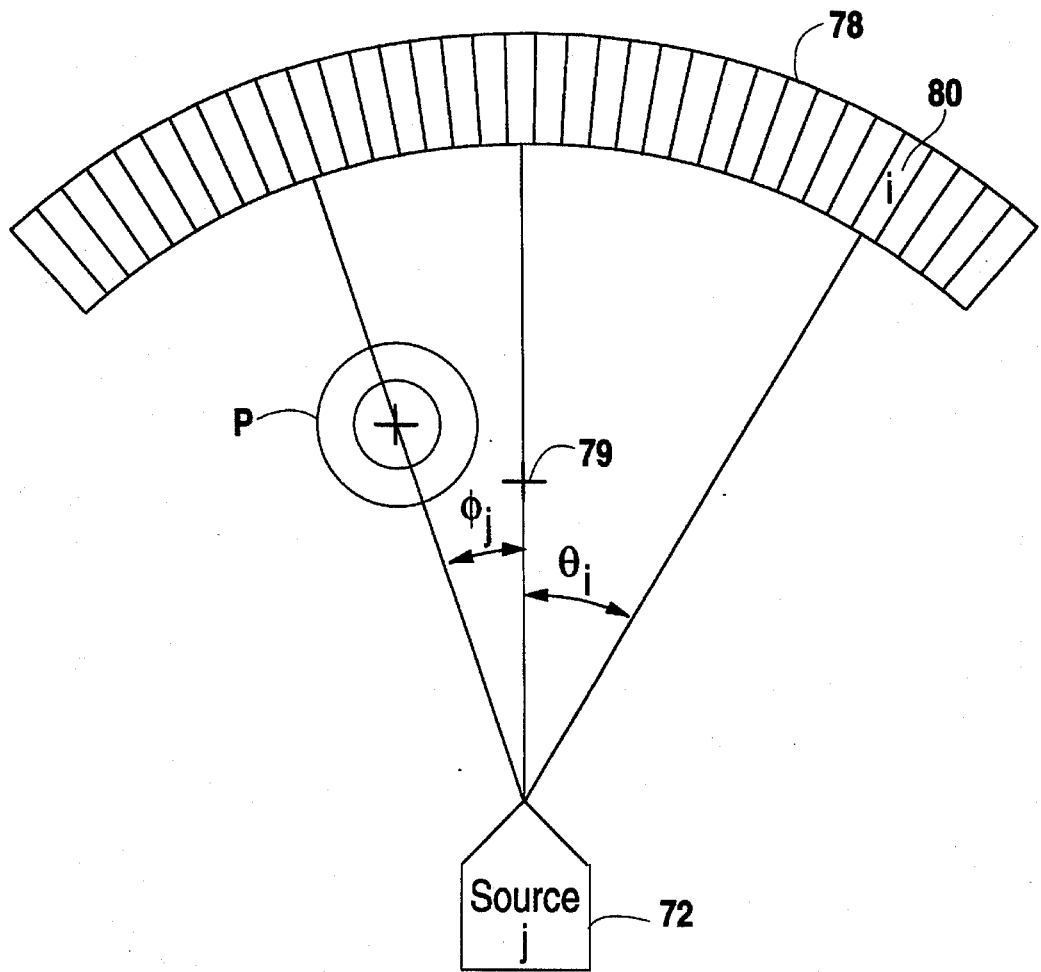
FIG. 7b is a simplified diagrammatic representation showing parameters used in the calculation algorithms.

The outside diameter and inside diameter calculations are executed by the coprocessor I program 142 in the main computer 120. The first calculation executed is to determine the angle to the tube P center, as seen by each of the three detector arrays 78. The calculation executed is:

$$\phi_j = 1/2 \text{ ARCTAN } \frac{2A_1A_5 - A_2A_4}{2A_3A_4 - A_2A_5}$$

where "$\phi_j$" represents the angle from source j 72 between the tube P center and the system center 79 (see FIG. 7b), "j" ranges from 1 to 3 (one for each detector array 78), "$L_i$" represents the path length as measured by the $i^{th}$ detector 80, and $$A1 = 1/2 [\Sigma_i \cos^2\Theta_i - 1/N(\Sigma_i \cos 2\Theta_i)^2]$$

$$A2 = \Sigma_i \sin 2\Theta_i \cos 2\Theta_i - 1/N(\Sigma_i \sin 2\Theta_i)(\Sigma_i \cos 2\Theta_i)$$

$$A3 = 1/2 [\Sigma_i \sin^2\Theta_i - 1/N(\Sigma_i \sin 2\Theta_i)^2]$$

$$A4 = \Sigma_i(L_i/2)^2 \cos^2\Theta_i - 1/N[\Sigma_i(L_i/2)^2 \cos 2\Theta_i]$$

$$A5 = \Sigma_i(L_i/2)^2 \sin^2\Theta_i - 1/N[\Sigma_i(L_i/2)^2 \sin 2\Theta_i]$$

where the summation extends over the four paths lengths, two on each side of the tube P and "$\theta_i$" represents the angle from source j 72 between the center of the $i^{th}$ detector 80 and the system center 79. (See FIG. 7b.)

Knowing the angle to the center of the tube P, as seen from each of the three detector arrays 78, it is possible to calculate the (x,y) center by triangulation between any pair of angles using the following formulas:

$$x_j = S_j \cos\Omega_j - D \cos(\phi_j + \Omega_j)$$

$$y_j = S_j \sin\Omega_j - D \sin(\phi_j + \Omega_j)$$

where ($x_j$, $y_j$) is the tube P outer diameter center location as determined for $j^{th}$ detector 80, "$S_j$" represents the distance from the apparatus center to $j^{th}$ source 72, "$\Omega_j$" is the angle from the system center between the $j^{th}$ source 72 and an arbitrary reference line, and:

$$D = \frac{DL + DP}{DD}$$

where $$DL = -\cos(\phi_{j+1} + \Omega_{j+1})(S_{j+1} \sin\Omega_{j+1} - S_j \sin\Omega_j)$$

$$DP = -\sin(\phi_{j+1} + \Omega_{j+1})(S_{j+1} \cos\Omega_{j+1} - S_j \cos\Omega_j)$$

$$DD = -\sin(\phi_j + \Omega_j)\cos(\phi_{j+1} + \Omega_{j+1})$$
$$\phantom{DD =} -\cos(\phi_j + \Omega_j)\sin(\phi_{j+1} + \Omega_{j+1})$$

After the above calculations have been completed, the outside diameter as seen by each detector array 78, "j" can be calculated as follows:

$$O.D._j = 2 DC_j [(TUL_j - TUR_j)/DEN_j]^{1/2}$$

where $$DC_j = [(S_j \cos\Omega_j - x_j)^2 + (S_j \sin\Omega_j - y_j)^2]^{1/2}$$

-continued $$TUL_j = \Sigma_i(L_i/2)^2 \{3N - 4[(\cos 2\phi_j \Sigma_i \cos 2\Theta_i) +$$
$$(\sin 2\phi_j \Sigma_i \sin 2\Theta_i)] + (\cos 4\phi_j \Sigma_i \cos 4\Theta_i) + (\sin 4\phi_j \Sigma_i \sin 4\Theta_i)\}$$

$$TUR_j = 2F_1F_2$$

$$DEN_j = 4[\Sigma_i(L_i/2)^2 F2_j - NF1_j]$$

and $$F1_j = \Sigma_i(L_i/2)^2 - (\cos 2\phi_j \Sigma_i(L_i/2)^2 \cos 2\Theta_i) -$$
$$(\sin 2\phi_j \Sigma_i(L_i/2)^2 \sin 2\Theta_i)$$

$$F2_j = N - (\cos 2\phi_j \Sigma_i \cos 2\Theta_i) - (\sin 2\phi_j \Sigma_i \sin 2\Theta_i)$$

Knowing the outside diameter enables a prediction of the shadow or path lengths that would be caused by a solid bar with the same outside diameter. The measured path lengths are subtracted from the solid bar path lengths and the inner circle (x, y) center and the inside diameter are determined in the same manner as the outer circle center and the outside diameter were determined, supra.

COPROCESSOR II MANAGER

Figure 10:
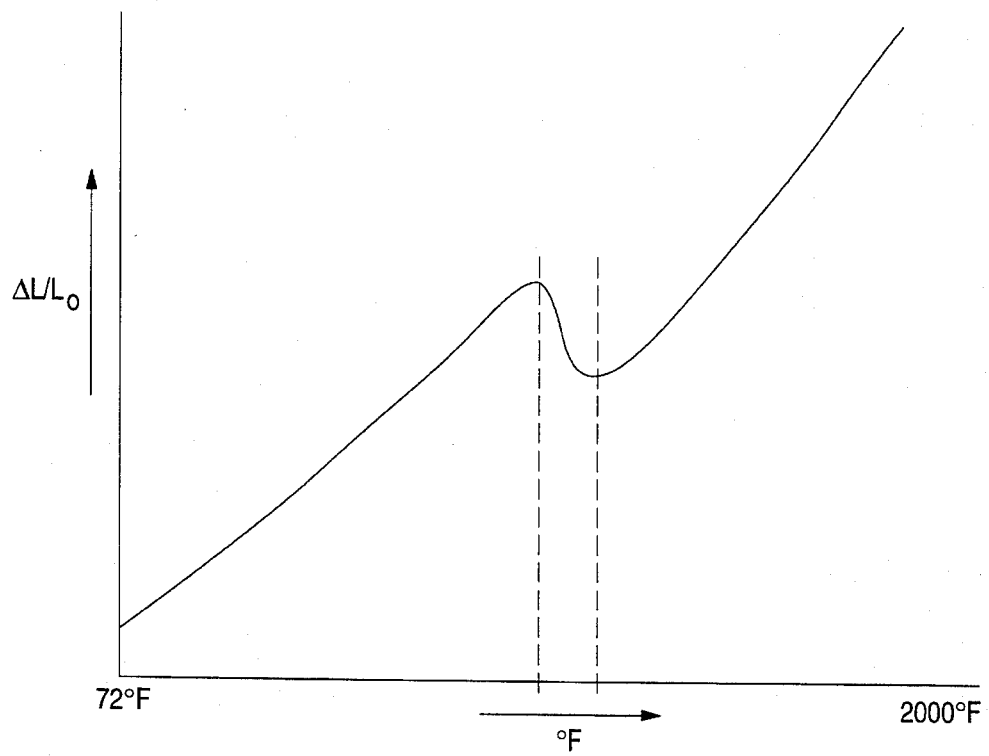
FIG. 10 is a graphic representation of a sample dilatometry curve used by the computer system to calculate ambient temperature dimensions of products measured at elevated temperatures.

In order to get fast feedback to the production process shown in FIG. 1, it is often necessary to measure the tube P while it is still hot. However, the hot dimensions of steel tube are not the same as the cold dimensions of the tube. Steel shrinks along what is commonly called a dilatometry curve, an example of which is shown in FIG. 10. Moreover, these dilatometry curves are not the same for all material compositions. For example, the percent carbon content in steel is an important factor in determining the dilatometry curve for different batches of steel. Consequently, a formula used to fit a dilatometry curve will vary depending on the material composition of the product. In the preferred embodiment of the invention, a curve fitting the dilatometry curve to obtain a formula which can be used to correct the hot temperatures is performed outside the computer system 46, the dilatometry curve fit formula is entered into the computer, via the display program 150. In the preferred embodiment, the calculation is performed in coprocessor II 124.

The main purpose of coprocessor II manager 144 is to send and retrieve sets of data to and from coprocessor II 124. In the process of performing this task, the coprocessor II manager 144, monitors the status flags 138 to determine when a set of data has been completed by coprocessor I 122 and ready to be sent to coprocessor II 122 for further processing. Likewise, the coprocessor II manager 144 raises a status flag 138 to signal the coprocessor III manager program 146 that coprocessor II 124 has completed its task. The data which is sent by the coprocessor II manager 144 to coprocessor II 122 includes: the hot temperature measurement of OD, ID, wall thickness, eccentricity, ovality; data from the object detectors 30; and data from the pyrometers 40. In addition, the coprocessor II manager 144 also sends the batch-specific dilatometry curve fit formula data which was entered into the shared common 132, via the display program 150 as described above.

Once the data has been received, coprocessor II 124 calculates the temperature measured by each pyrometer 40. This calculation is performed by converting the electronic signal of each pyrometer 40 using a conventional linear conversion algorithm. Coprocessor II 124 also calculates the average temperature for each cross-section of the tube P and the average temperature of the whole tube P using a conventional averaging algorithm. Coprocessor II 124 also calculates the average OD and ID for each cross-section of the tube. These averages are needed to calculate cross-sectional ovality and eccentricity.

The ovality, which is defined by the dimensional difference between maximum and minimum outside diameter as rotated around the circumference of the tube P, is calculated after computation of the average outside diameter and inside diameter for each sectional along the length of the tube P. It is assumed that the outer surface, "S" of the tube P can be described by an average radius, "R", that is modulated by a sine function of amplitude, "A" such that:

$$S(\theta) = R + A(\sin 2\theta)$$

The ovality is then defined as 2A. Since there are multiple measurements, one for each detector array 78, a chi-squared fitting technique can be applied to solve for A.

Eccentricity is determined by using the (x, y) centers calculated by the coprocessor I program 142. The eccentricity is physically defined as the dimensional displacement of the center of the outer surface of the tube P from the center of the inner surface of the tube P. The average (x,y) centers for both outside diameter and inside diameter for each section along the tube P are calculated. The averages are then vectorially subtracted from each other to find the total displacement:

$$D = SQRT[(X_{OD}-X_{ID})^2 + (Y_{OD}-Y_{ID})^2]$$

where "$(X_{OD}, Y_{OD})$" is the average co-ordinate for the outer surface center, "$(X_{ID}, Y_{ID})$" is the average co-ordinate for the inner surface center, and "D" is the displacement between the two average center co-ordinates.

After the ovality, eccentricity and minimum wall thickness have been calculated, coprocessor II 124 takes the hot temperature measurements of the tube P and calculates/ predicts the anticipated cold temperature dimension of the tube P. The cold dimensions of the tube P are calculated/ predicted using the following formula:

$$D_c = F(D_h)$$

where "$D_c$" is the cold temperature dimension, "$D_h$" is the hot temperature dimension, and "$F(D_h)$" is the function which was input into coprocessor II 124 by the coprocessor II manager 144, representing the function which was form fit to the dilatometry curve of the material from which the scanned object is made.

Coprocessor II 124 has several functions in addition to its primary function of calculating ovality, eccentricity and dilatometry corrections. The coprocessor II 124 also determines the length and velocity of the tube P. To perform these tasks, coprocessor II 124 depends on information from a series of object detectors 30 along the production path of the tube P. These detectors 30 turn on when they detect the presence of tube P and they turn off when the tube P is no longer present. Two velocity measurements and an average velocity measurement are calculated using the following formulas:

$$V_2 = [D_j - D_{j+1}]/[T_j - T_{j+1}]$$

$$V_1 = [D_i - D_{i+1}]/[T_i - T_{i+1}]$$

$$V = [V_1 + V_2]/2$$

where "i" represents the detector 30 that records the front of the tube P, "j" represents the detector 30 that records the end of the tube P, "$T_i$" represents the time recorded when the front end of the tube P passes the $i^{th}$ detector $30_i$, "$T_{i+1}$" represents the time recorded when the front end of the tube P passes the detector $30_{i+1}$ immediately following the $i^{th}$ detector $30_i$, "$D_{i+1}$" represents the location of the $i^{th}$ detector $30_i$, "$D_{i+1}$" represents the location of the detector $30_{i+1}$, immediately following the $i^{th}$ detector $30_i$, and "$V_1$" represents the velocity of the front end of the tube P. "$T_j$" represents the time recorded when the trailing end of the tube P passes the $j^{th}$ detector $30_j$, "$T_{j+1}$" represents the time recorded when the trailing end of the object passes the detector $30_{j+1}$, immediately following the $j^{th}$ detector $30_j$, "$D_j$" represents the location of the $j^{th}$ detector $30_j$, "$D_{j+1}$" represents the location of the detector $30_{j+1}$, immediately following the $j^{th}$ detector $30_j$, and "$V_2$" represents the velocity of the trailing end of the tube P.

"V" represents the average tube P velocity.

From these calculations, the tube P length, "L", is calculated using the following formula:

$$L=[D_i-D_{j1}+V*[T_i-T_j]$$

If the tube P velocity changes, then the formula is modified in discrete increments to account for this change.

After coprocessor II 124 has completed calculating the temperature, cold temperature dimensions and the length and velocity of the tube, information is picked by the coprocessor II manager which places all of the results in the shared common to make the results available for use by the other programs of the system.

COPROCESSOR III MANAGER

The main purpose of the coprocessor III manager 146 is to send and retrieve sets of data to and from coprocessor III 126. In the process of performing this task, the coprocessor III manager 146 monitors the status flags 138 to determine when the set of data is complete by coprocessor II 124 and ready to be sent to coprocessor III 126 for further processing. Likewise, the coprocessor III manager 146 raises a status flag 138 to signal to the other programs that it has completed its tasks. The data which is sent by the coprocessor III manager 146 to coprocessor III 126 includes: the calculated/predicted cold temperature dimensions of the tube P and the desired dimensions of the ideal tube. In addition, coprocessor III 126 also receives dimensional characteristics of various components of the manufacturing process. For example, the outer diameter ("OD"), inner diameter ("ID"), velocity, pressure and gap distances of all the rollers in the manufacturing process; the temperature of the tube P at various stages of the manufacturing process; and the OD of the components piercer 6, elongator 7, plug mill 8 and reeler 9 involved in shaping the inner surface of the tube P.

Coprocessor III 126 calculates the variance between the measured cold temperature dimensions of the actual tube P and the desired dimensions of an ideal tube. These variances represent flaws in the tube P. The calculations include variances in: OD, ID, wall thickness, eccentricity and ovality. From these variances, coprocessor III 126 generates control signals which modify the manufacturing process to correct the flaws and prevent production of the same flaws in the future.

The characteristics of the variances found determine the control signals which are generated by coprocessor III 126. The signals which are generated are unique to the manufacturing process in which the apparatus A is integrated. In the disclosed embodiment, these control signals are directed to conventional motors 60 or other types of actuators, which affect a variety of manufacturing step variables. These motors 60 control the position of the rollers thereby setting the gap distance between the rollers. When several sets of rollers work in tandem, the position of the roller can have an additional affect on the pressure exerted by the roller on a workpiece. The motors 60 are also used to control rotational speed profile of the rollers. Additionally, the position of the piercer 6 is also controlled by motors. Coprocessor III 126 also generates control signals which are utilized in the rotary furnace's 5 control algorithm to adjust the temperature in the rotary furnace 5, quench furnace 12 and temper furnace 14. In situations where coprocessor III 126 identifies a variance whose cause cannot be automatically corrected, it generates a signal to the operator providing information concerning the flaw and its probable cause or causes.

Figure 9A:
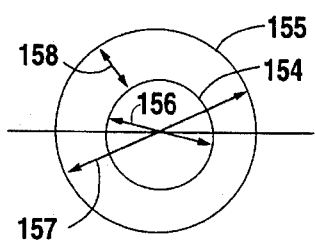
Figure 9B:
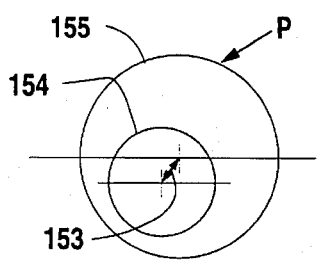

Consider a variance in the form of eccentricity 153 (FIG. 9b) between the inner surface 154 and the outer surface 155 of a tube P. If an unacceptable level of eccentricity 153 is found, coprocessor III 126 generates a control signal that is transmitted to motors and thermostats that control the piercer 6 and rotary hearth furnace 5. Correction algorithms developed for particular drive systems are provided by coprocessor III 126. Motors 60 will reposition the piercer 6 so that it does not cause the same error again. If the eccentricity 153 variance follow a pattern along the length of the tube, coprocessor III 126 generates a signal to the piercer 6 if motors 60 adjustment is possible. However, if the pattern is not-correctable through feedback to the piercer 6, coprocessor III 126 generates a signal to the operator providing information concerning the variance and its cause.

If coprocessor III 126 discovers an unacceptable degree of ovality (FIG. 9e), then it generates a signal to the motors 60 which set the gap distance between the rollers at the elongator 7, plug mill 8 and finish mill 15. The proportion of modification between these processing steps is a function of the degree of ovality.

If coprocessor III 126 finds a variance at ID 156 (FIG. 9a), then it compares the plug sizes, gap spacing and the roller pressures of the plug mill 8 and high mill 10. If a variance is determined to be caused by roller pressures or gap spacing, then coprocessor III 126 generates a signal to the motors 60 which adjust the position of the rollers in the plug mill 8 and/or high mill 10. However, if the coprocessor III 126 determines that plugs are causing this variance, then it will generate a signal to the operator recommending replacement of the plug.

Similarly, if coprocessor III 126 finds a variance on OD 157 (FIG. 9a), then it compares the gap spacing and the roller pressures at the plug mill 8, high mill 10, and finishing mill 15. Based on the size of the variance, coprocessor III 126 generates signals to the roller motors 60 to modify the roller pressures and gap spacing of the rollers at the plug mill 8, high mill 10, and finishing mill 15. If the variance is small, most of the adjustment is made to the rollers in the finishing mill 15; if the variance is large, most of the adjustment is made to the rollers in the plug mill 8 and high mill 10.

Related to finding a variance in both the OD 157 and ID 156 (FIG. 9a), coprocessor III 126 also identifies variances in the wall thickness 158. If a variance is found, coprocessor III 126 compares the plug sizes, gap spacing and roller pressures at the plug mill 8 and high mill 10. Coprocessor III 126 then generates a signal to the motors 60, which control the roller pressure and gap spacing in the plug mill 8 and high mill 10 and, if necessary, generates a signal to the operator that a plug may need to be replaced.

In addition to calculating variances and generating control signals concerning the general cross-sectional dimensions of the tube P, coprocessor III 126 also examines the pattern of localized variances in wall thickness 158 (FIG. 9a) along the length of the tube P. In performing this analysis, coprocessor III 126 identifies potential causes of these localized variances. One characteristic typically found in manufacturing processors, which involve rolling of a workpiece, is a periodic flaw as shown in FIG. 9f. These periodic flaws are typically caused by rollers which have worn irregularly or have an external flaw or imbedded debris. A flaw on a roller tends to cause periodic pits 159 on the outer surface of the tube. The period 151 of flaws is a function of the circumference and diameter of the roller that causes the flaw. Therefore, if coprocessor III 126 determines that the localized variance is periodic, it compares the period 151 of flaws with the OD and ID of all rollers in the manufacturing process. From the results of this comparison, the coprocessor III 126 generates a signal informing the operator of the periodic nature of the flaw and the roller which most likely caused the flaw.

Figure 9C:
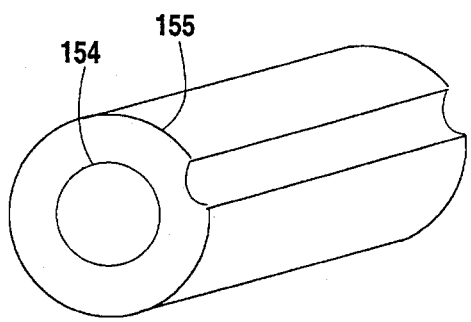
Figure 9D:
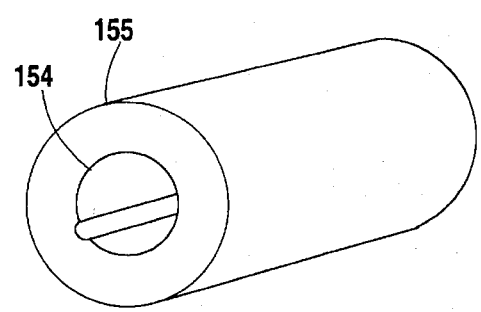
Figure 9E:
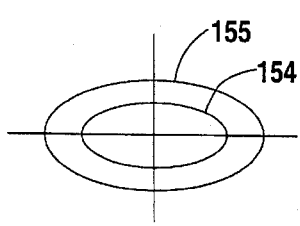
Figure 9F:
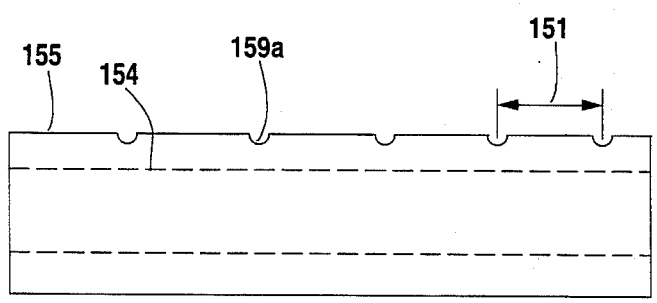

Coprocessor III 126 is also capable of discovering continuously longitudinal flaws along the length of the tube as shown in FIGS. 9c and 9d. If the flaw is on the inner surface 154 of the tube P, then it generates a signal that the plug in the plug mill 8 may need to be replaced. The plug in the plug mill 8 is the only possible cause for such a flaw. However, if the flaw is on the outer surface of the tube, identifying the probable cause of the flaw is more complicated. To identify the probable cause of a longitudinal flaw on the outer surface of the tube, coprocessor III 126 must find a periodic aspect to the variance and compare it to the roller OD's and ID's of the plug mill 8 and finishing mill 15. If a periodic aspect to the flaw can be found, then coprocessor III 126 can write a signal informing the operator of the flaw and which rollers are most likely to cause the flaw. Otherwise coprocessor III 126 simply generates a signal to the operator indicating the detection of a longitudinal flaw.

Figure 9G:
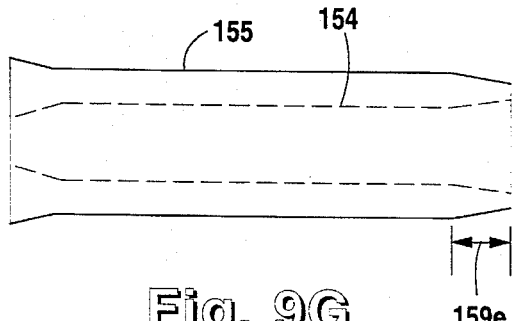
Figure 9H:
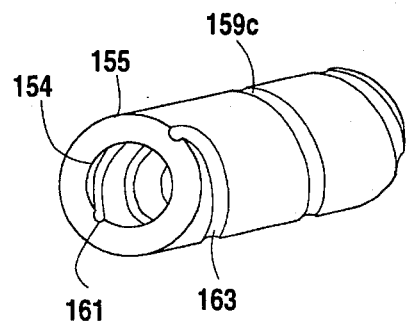

Coprocessor III 126 also identifies continuous spiraling flaws 161 on the inner surface 154 of the tube P as shown in FIG. 9h. Coprocessor III 126 identifies the cause of such flaws by comparing the flaw 161 to the velocity and length of the tube P and also the rate of rotation of the tube P in the piercer 6, elongator 7 and reeler 9 to determine which plug is causing the variance. Based on this comparison, coprocessor III 126 generates a signal informing the operator that the plug in the piercer 6, elongator 7 and/or reeler 9 must be replaced.

On the other hand, if coprocessor III 126 identifies continuous spiraling flaws 163 on the outer surface 155 of the tube P (FIG. 9h), identification of the cause is more complicated. In addition to the factors considered in the comparison which identifies the cause of the inner flaws 161, coprocessor III 126 also considers the OD of the rollers in the piercer 6, elongator 7 and reeler 9. Based on this comparison, coprocessor III 126 generates a signal informing the operator of a spiraling flaw 163 and which rollers most likely caused the flaw.

DISPLAY EAGER

A display program 150 provides user interface to the Apparatus (FIG. 2). Through the display program 150, the user has the ability to: 1) enter object specification and metallurgical chemistry data (including dilatometry data), 2) control the apparatus' operation, 3) review the measurement data in tabular form, 4) visually analyze fault conditions in graphic form, and 5) monitor the environmental and safety conditions of the apparatus while in operation. The display program is preferably menu driven to give the user easy access to information and the system control commands available to him.

The user is provided with means to enter ideal tube specifications such as: outside diameter, wall thickness, inside diameter, tolerances and grade of steel for dilatometry purposes. If the system does not already contain dilatometry data on the type of material to be used, this data can be entered as well. The display program will make this information to the shared common memory 132 in the main computer 120 for other programs to access.

The display program 150 provides for means to: 1) terminate and initiate processing of data, open and close the radiation sources 72, 2) adjust the sampling rate, and 3) set parsing interval spacing for data reduction in coprocessor I 122.

Several options are available for displaying the information generated by the apparatus A. It can be displayed either visually or on hard copy. For example, outside diameter verses tube length or wall thickness versus tube length or eccentricity verses tube length. The output can be either tabular or graphic. Out-of-specification longitudinal sections or cross-sections can be reconstructed and displayed on the video screen or on hard copy.

DATA ARCHIVE MANAGER

The data archive program 152 stores information in disk files and provides information for operator output. The program is cyclically activated whenever a tube P exits the apparatus A by monitoring a signal in the shared common memory 132 controlled by the data acquisition program 140. The data archive program 152 also calculates foot averages; tube averages; maximum and minimum OD's and ID's and wall thickness; and other tube summary information for each tube P that is scanned and for the entire batch of tubes in a run-of-the-mill. The display program 152 also provides output to the operator in the form of printed information or graphic displays on either the computer display screen or through a printer.

The tube production process, which the preferred embodiment of the Apparatus is intended to control, allows for a sufficient time interval between tubes P to permit the main computer to perform these calculations. If the production process was continuous, these calculations could be dedicated to additional coprocessors, since there would be no time interval in which to perform these calculations. The structure of the Apparatus has sufficient flexibility to adapt to different production processes in order to maximize efficiency and minimize equipment cost.

CALIBRATION

In addition to the computer programs described above, the Apparatus includes a calibration program. Calibrating the apparatus A is essential to obtaining accurate results. The calibration program for this particular embodiment performs two separate and independent calibrations: one calibration determines geometric parameters of the source/detector apparatus 32, and the other calibration determines the path length quadratic correction parameters for each detector 80, the use of which was described previously.

Figure 11:
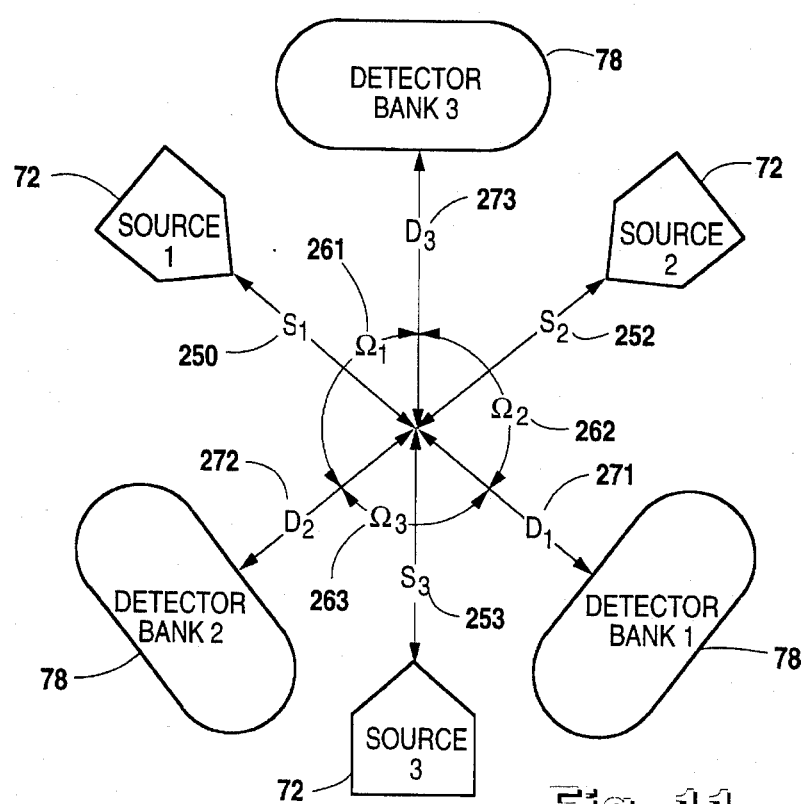
FIG. 11 is a simplified diagrammatic representation of the parameters used by the computer system to calibrate the apparatus to account for the geometry of the source/detector apparatus.

Since the preferred embodiment contains at least three source and detector array pairings 70, the geometry of the source/detector apparatus 32 (FIG. 11) is defined in ten parameters which are all measured from the source/detector apparatus' center: three parameters 251, 252 and 253 define the distances 51, 52 and 53 of each source 72 from the center, three parameters 261, 262 and 263 define the angles $\Omega_1$, $\Omega_2$, and $\Omega_3$ between the three detector arrays 78, three parameters 271, 272 and 273 define the distances $D_1$, $D_2$ and $D_3$ of each detector array 78 from the center of the apparatus A, and one parameter (not shown) defines the interdetector spacing between each detector 80 in the detector array 78.

Figure 12:
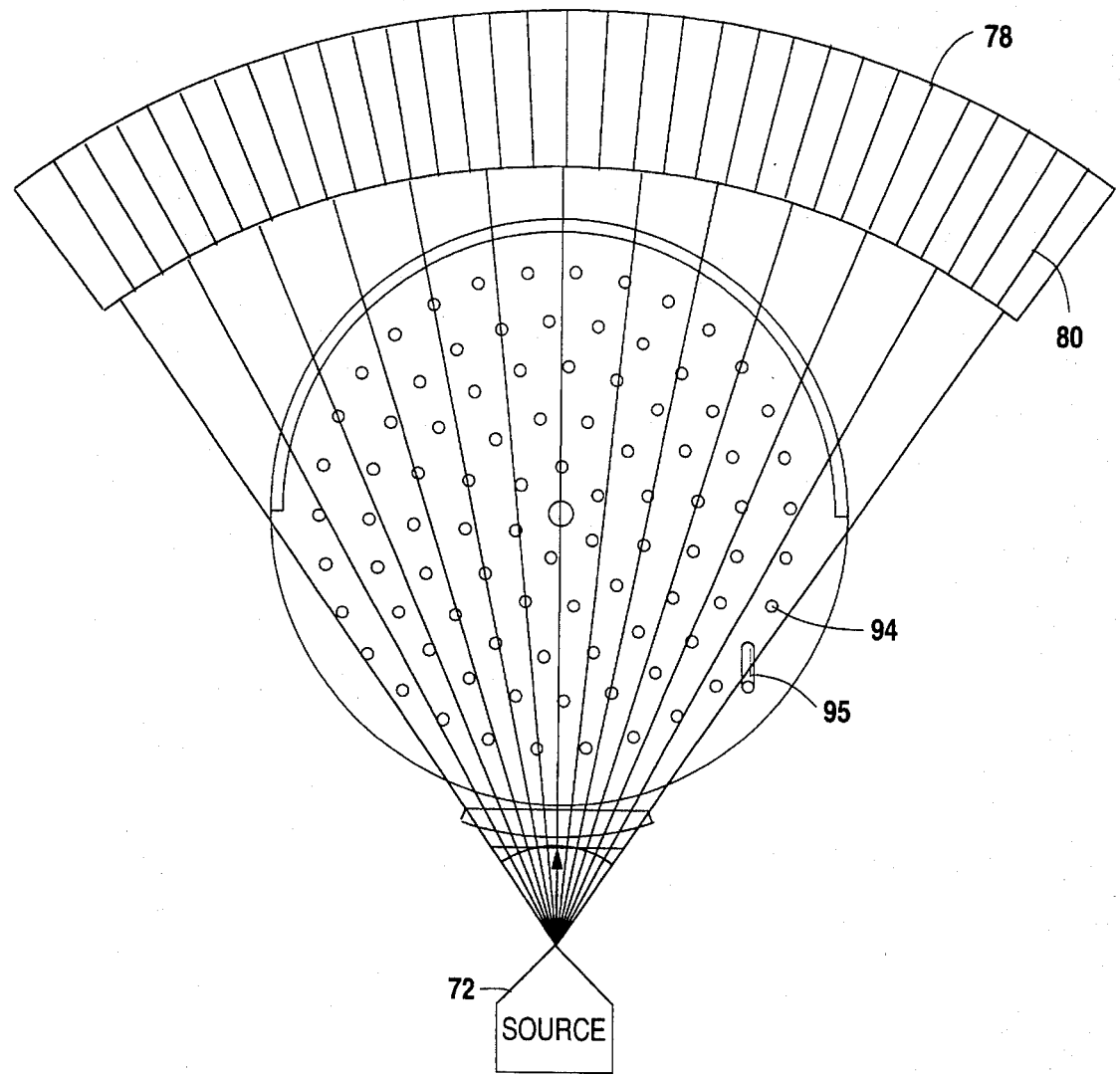
FIG. 12 is a simplified diagrammatic representation of a calibration plate in position between a source and detector array which is used to calibrate the geometrical relationship between the sources and detector arrays.

The method used to determine these parameters involves a calibration plate 94 (FIG. 12) which can position a steel bar 95 in a multitude of known calibrated locations 96. The preferred embodiment utilizes a calibration plate/steel bar design with 91 different calibrated locations 96. After a measurement has been taken by the apparatus A for each of the locations, a chi-squared minimization is performed by the geometry parameter calibration program to determine the ten geometric parameters of the apparatus A.

The second calibration performed by the calibration program is designed to normalize the path length calculation from one detector 80 to another in order to have consistent results as the tube P varies from the center of the scanning apparatus. This calibration is necessary because the tube P is not held in place and varies in its position within the apparatus as it moves through it. The formula used to normalize the path length is the following:

$$L' = X + (Y)(L) + (Z)(L)^2$$

Figure 13:
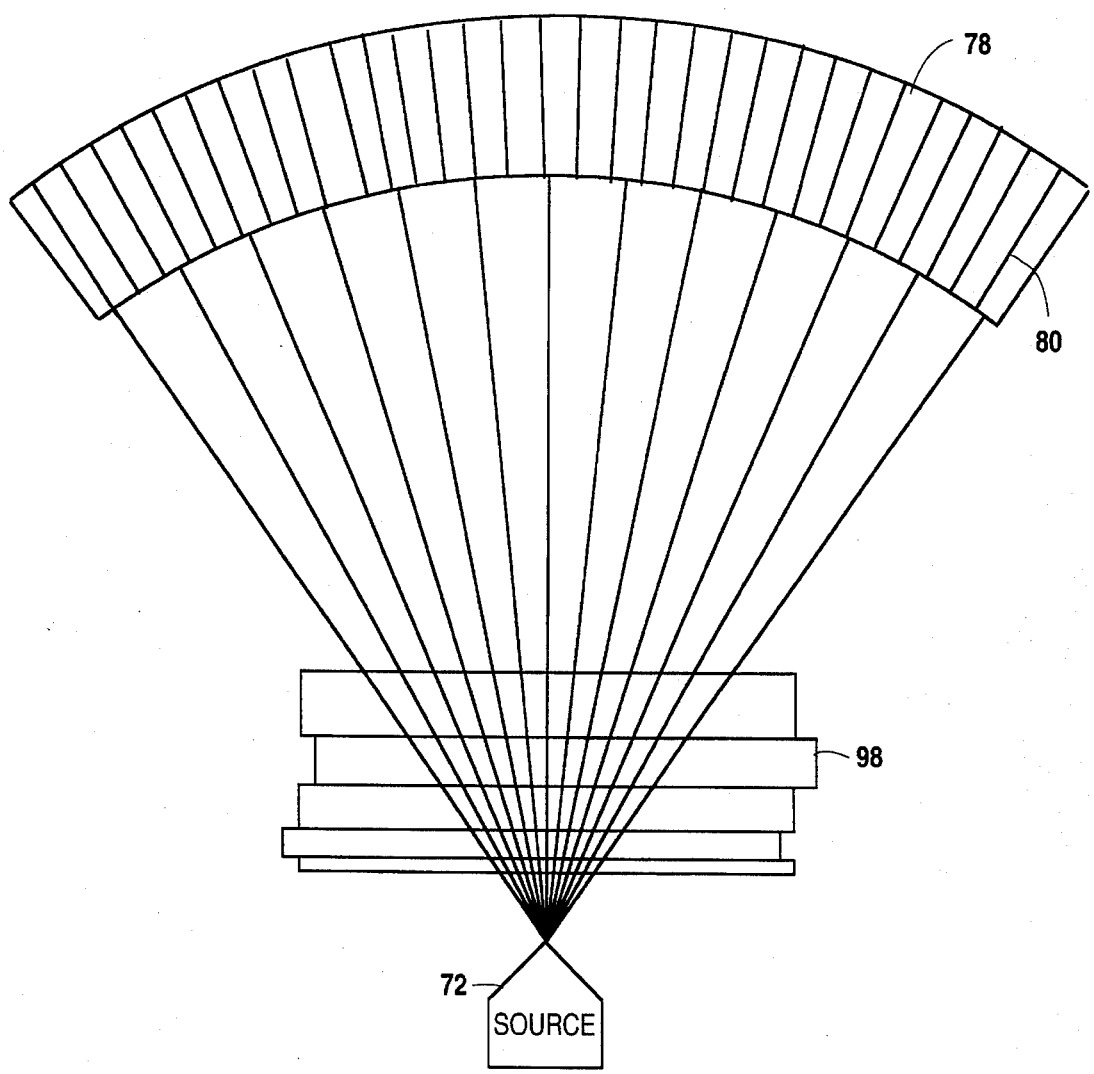
FIG. 13 is a simplified diagrammatic representation of other calibration plates of varying thickness in position between a source and detector arrays which are used to calibrate the individual detectors of the detector array.

Each detector 80 has a unique "$X_i$", "$Y_i$", and "$Z_i$" which is calculated and determined by the calibration program. The method used to determine these parameters involves a set of steel plates 98 (FIG. 13) that vary in thickness from 0.5 inches to 5.5 inches, in 0.5 inch increments. After unnormalized measurements are taken for each plate, a chi-squared minimization is performed to determine the normalization parameters "$X_i$", "$Y_i$", and "$Z_i$" for each detector 80. These parameters are used later in the coprocessor I program 142 where path lengths are calculated during normal operation.

OPERATION

The following description of the data flow and the graphical representation of the same in FIG. 8 is only representative. As mentioned previously herein, the programs described herein do not necessarily run in any particular order. In fact, they often run at the same time. For example, while the coprocessor II manager 144 is detecting flaws from the first set of cross-sectional data, the coprocessor I manager 142 may be processing the second set of cross-sectional data or possibly the data acquisition manager 140 may be collecting the third set of cross-sectional data.

The presence of tube P is detected by object detectors 30. In step 500, the source/detector apparatus 32 begins to emit and detect gamma ray signals. In step 502, the presence of tube P in the path of the gamma rays 74 causes the gamma ray signal to be attenuated. In step 504, detectors 80 transform the gamma ray signal to electrical signals. In step 506, the signals from the detectors 80 is conditioned by the detector signal conditioning subassembly 42 and collected and counted by the data acquisition control system 44. In step 508, the data acquisition control system 44 and 507 make sets of data available to a high speed low noise communication link 48 to the computer system 46. In step 510, the data acquisition manager program 140 in the main computer 120 place the raw digital data into partition 134 of the shared common memory 132 of the main computer 120.

Five programs previously described take turns monitoring the status flags 138 in the shared common 132. These programs include: the display program 150, the coprocessor I manager 142, the coprocessor II manager 144, the coprocessor III manager 146 and the data archive program 152. The display program 150 serves as the operator interface to the computer system 46. It can be used to access any information in either the shared common 132 or the long term memory device 129 and 511. The display program can instruct this information to be displayed at the operator's option 512. For the sake of simplicity, this description of the data flow discussion will trace a single set of cross-sectional data through the main computer programs, coprocessors, and coprocessor programs.

After all the raw data is collected, in step 516 a status flag 138 is raised calling the coprocessor I manager program 142 into action. In step 518, the coprocessor I manager 142 sends the raw data from partition 134 to coprocessor I 122. If the presence of tube P is detected in step 520 (FIG. 8b), in step 522, coprocessor I 122 receives the raw data 134 from the shared common 132 (FIG. 8b). In step 524, coprocessor I 122 performs path length calculations and reduces the raw data 134. In step 526, coprocessor I 122 uses the path length calculation results to calculate outside diameter, inside diameter, wall thickness and (x,y) centers for each OD and ID measurement. In step 528, coprocessor I 122 sends the results to the coprocessor I manager 142, which in turn, in step 518, places the results in partition 136 of the shared common memory 132. When the results from coprocessor I 122 are placed in the shared common 132, a status flag 138 is raised in the shared common 132 in step 530.

When the status flag 138 is raised, the coprocessor II manager sends data to coprocessor II 124 in step 532. In steps 534 and 136 (FIG. 8c) coprocessor II receives metallurgical chemistry data, including a formula fit to the material's dilatometry curve, and also temperature data from the pyrometers 40; and position data from the object/position detectors 30; and the hot temperature measurements of OD, ID, and wall thickness calculated in coprocessor I 122. In step 538, coprocessor II 124 calculates average OD, ID and temperature of the three pyrometer 40 readings for each cross-section along the length of the tube P.

In step 540, using the cross-sectional averages of OD and ID, coprocessor II 124 calculates the ovality and eccentricity of the cross-section of the hot tube P. In step 542, using the measured dimensions of hot tube P and the cross-section average temperature, and the material-specific dilatometry curve-fit function, coprocessor II 124 calculates the cold temperature dimensions of the tube P In step 544, coprocessor II 124 also calculates tube velocities and differential tube velocity using the data collected by the position/object detectors 30. Finally, in step 545 coprocessor II 124 makes all of the results available to the coprocessor II manager program 144. In step 532 (FIG. 8a), the results 136 from coprocessor II 124 are placed in shared common 132. In step 548, a flag is raised signalling the coprocessor III manager program 146 to begin. Similar to the previous coprocessor manager programs, in step 550 the coprocessor III manager 146 sends data to and from coprocessor III 126. In step 552 (FIG. 8d), coprocessor III 126 receives the calculated cold dimensions of the tube P and the desired dimensions of an ideal tube. In step 554, coprocessor III 126 also receives dimensional characteristics of various manufacturing steps, including rollers, outer diameters, inner diameters, velocity and pressures; the temperature of the rotary furnace 5, piercer 6, elongator 7, plug mill 8, high mill 10, temper furnace 14 and finishing mill 15; and outer diameters of the piercer and plugs. In step 556, using the actual and ideal dimensions of the tube, coprocessor III 126 calculates variance in OD, ID, wall thickness, eccentricity and ovality.

Figure 8A:
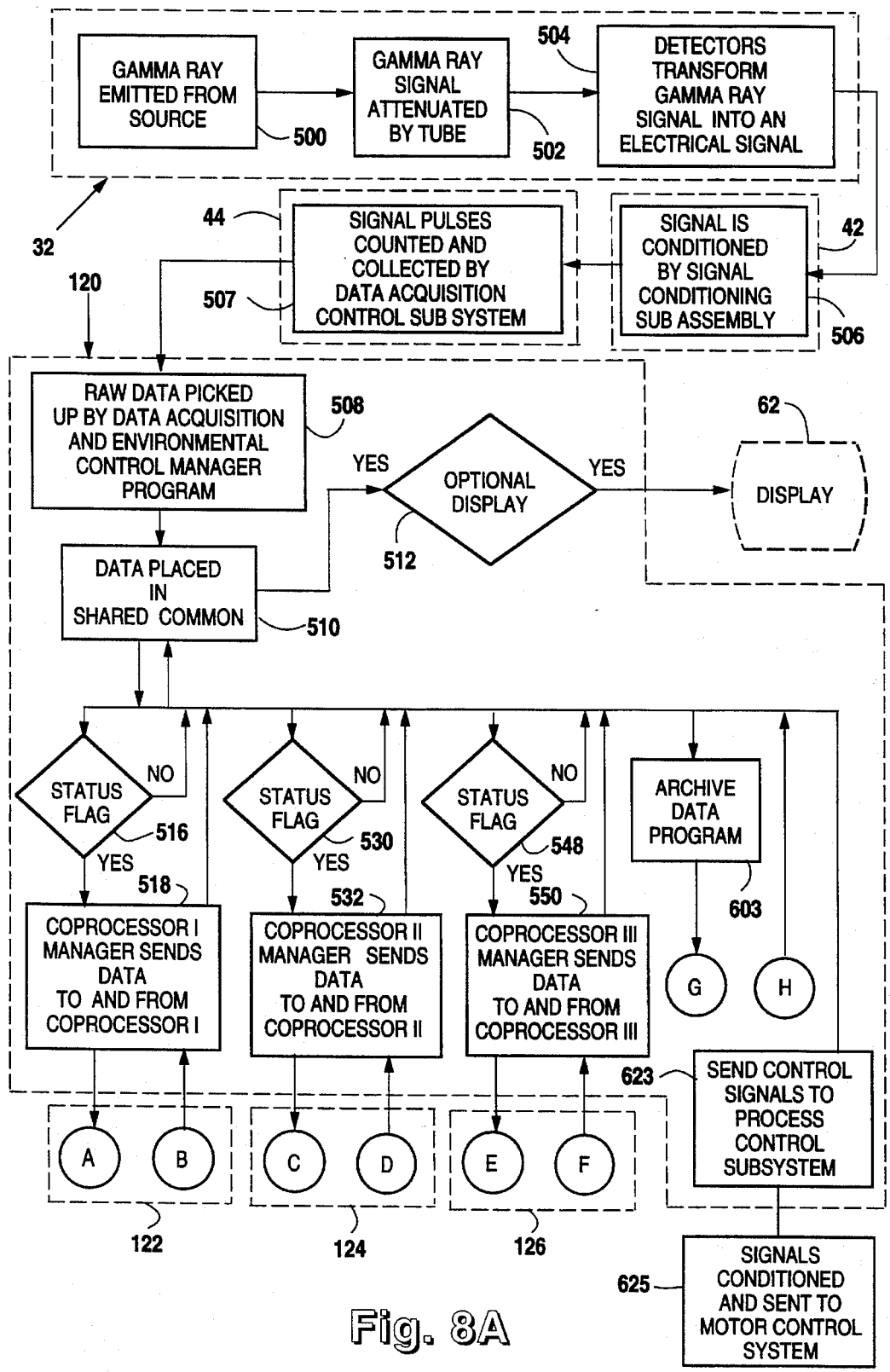
Figure 8D:
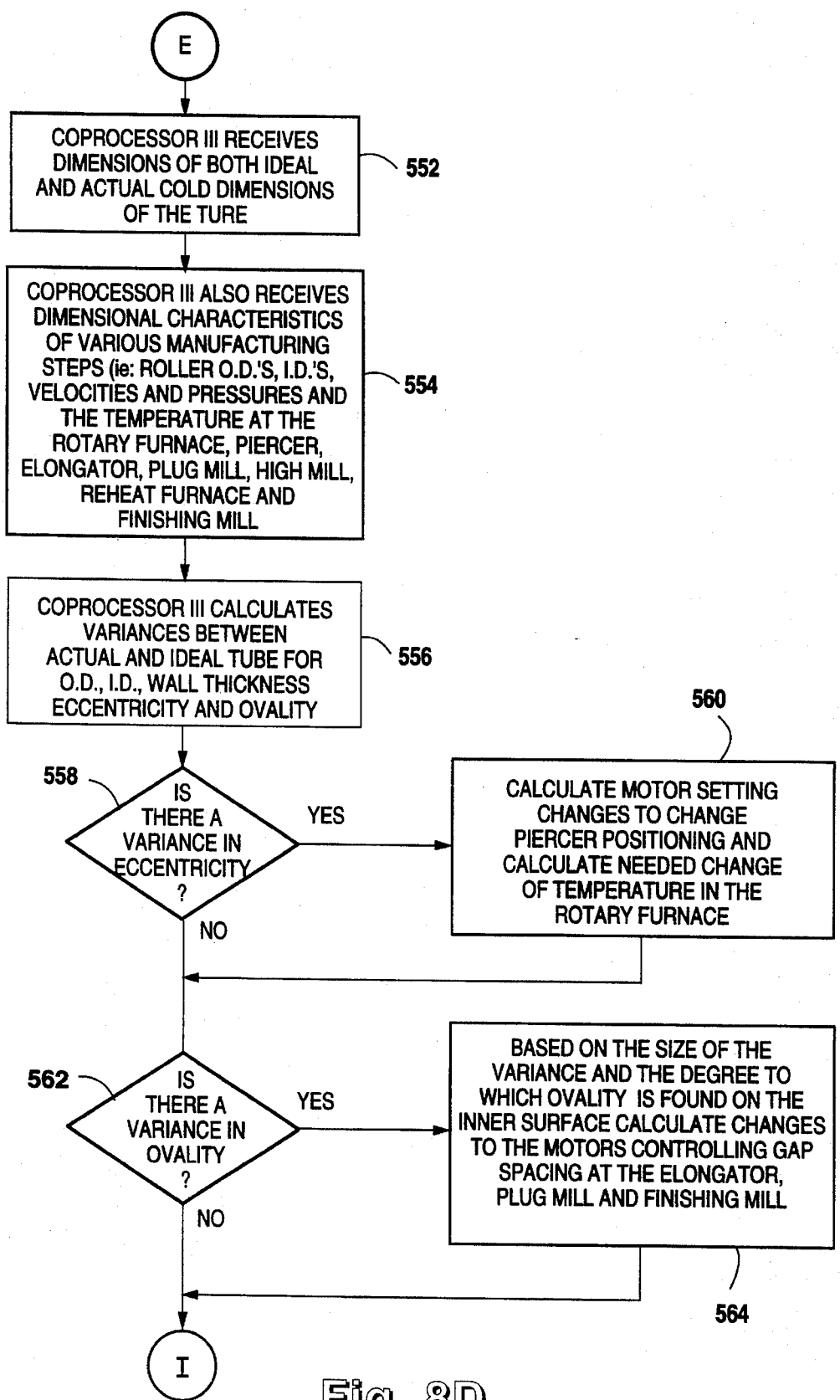
Figure 8E:
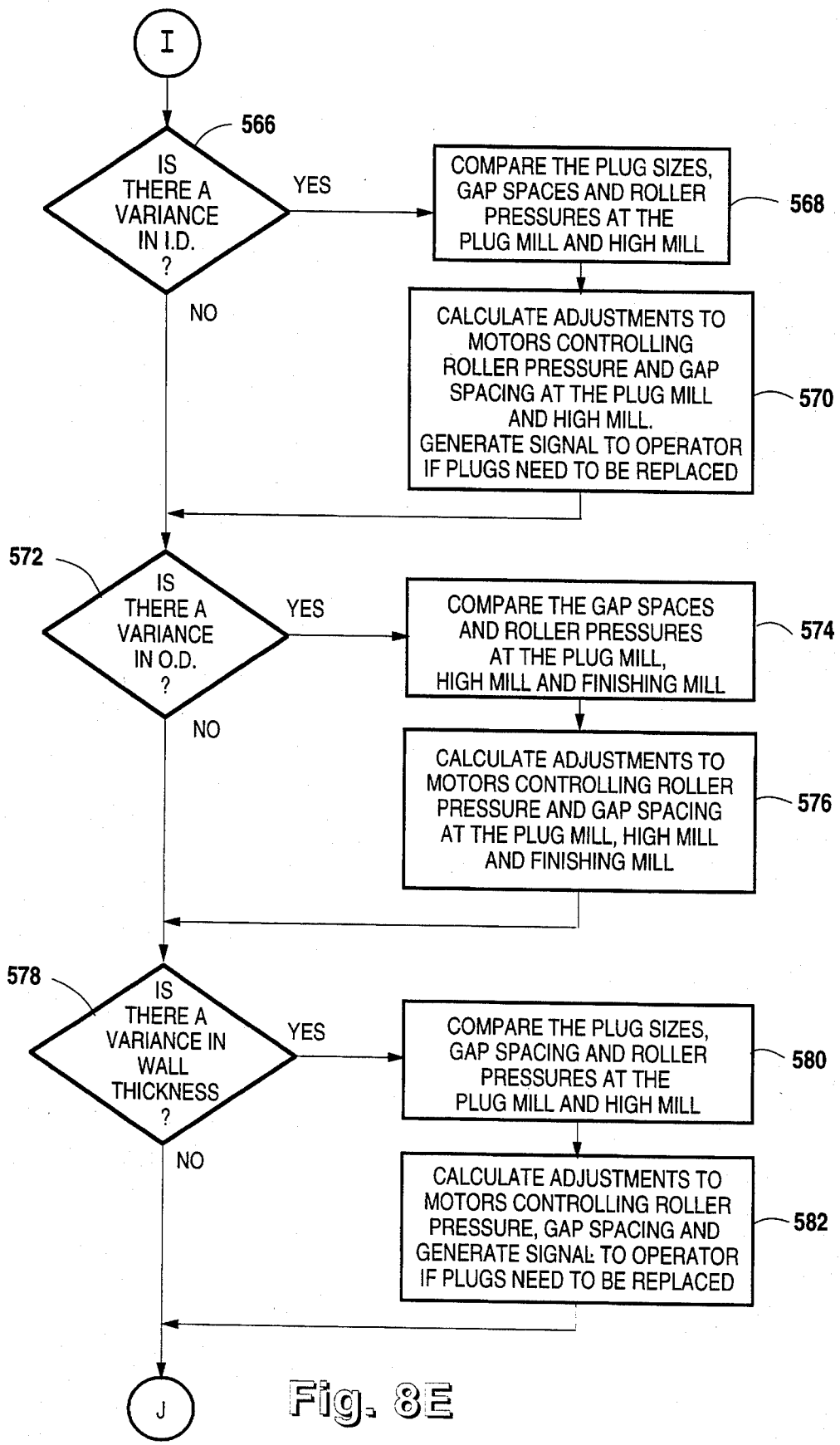
Figure 8F:
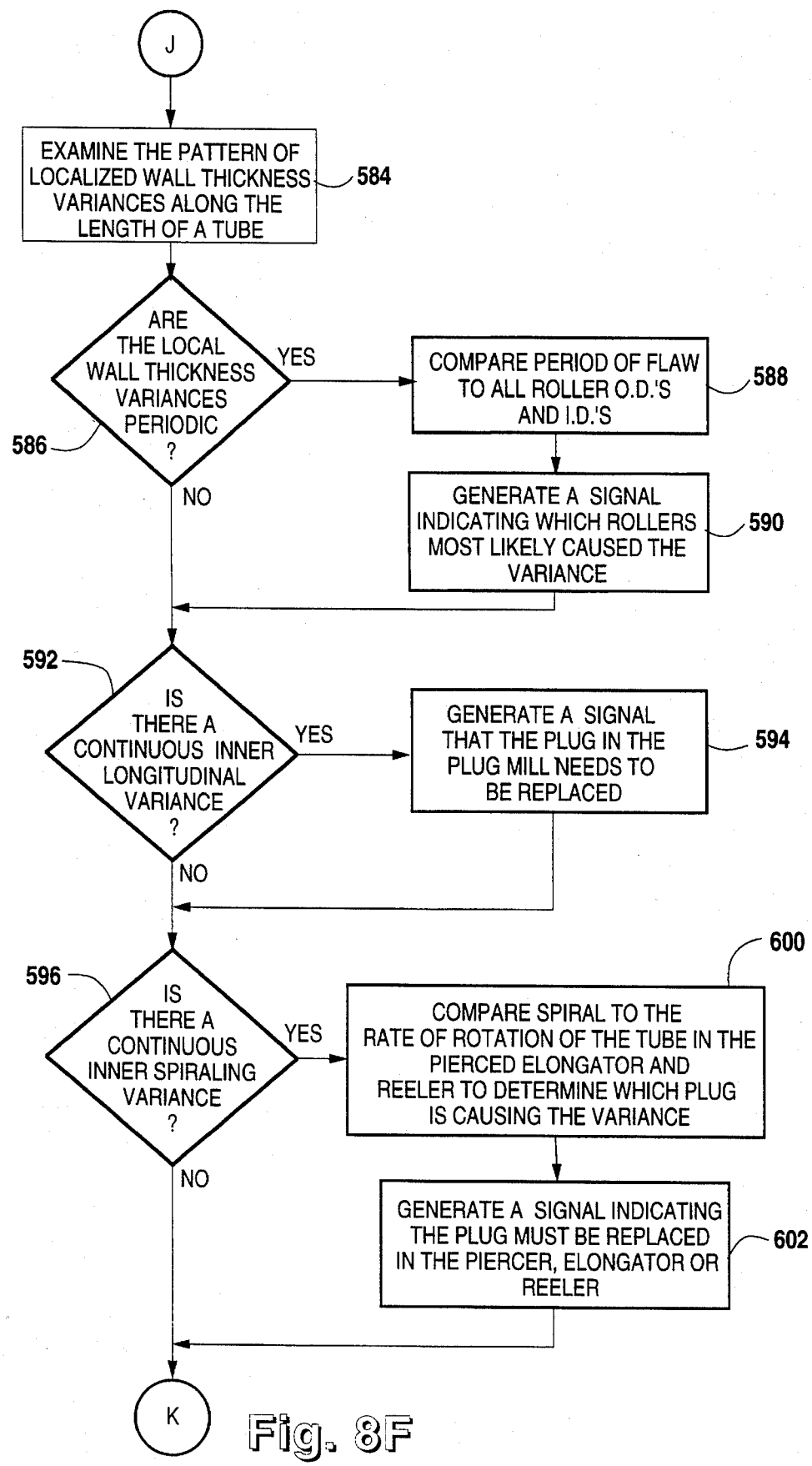
Figure 8G:
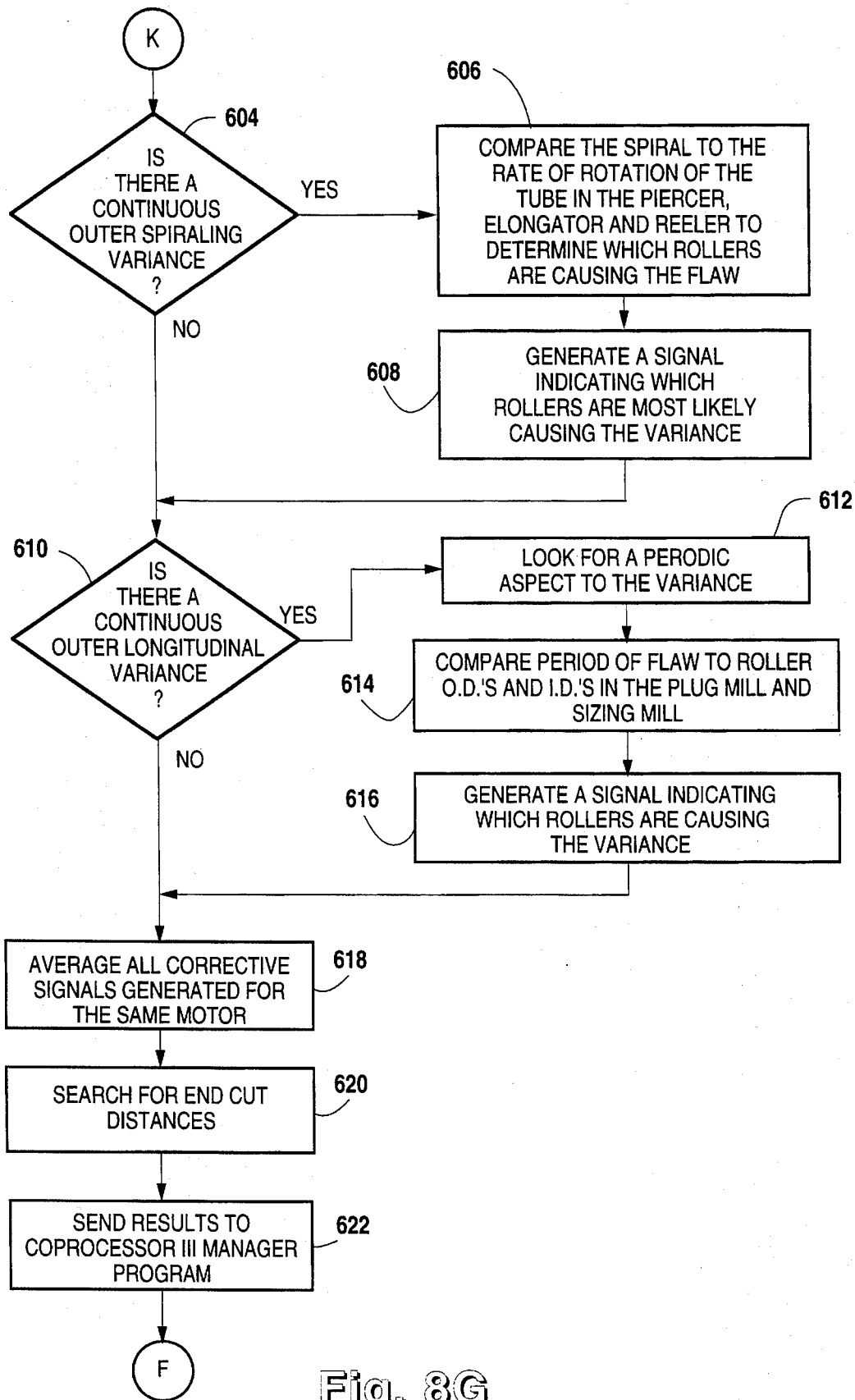
Figure 8H:
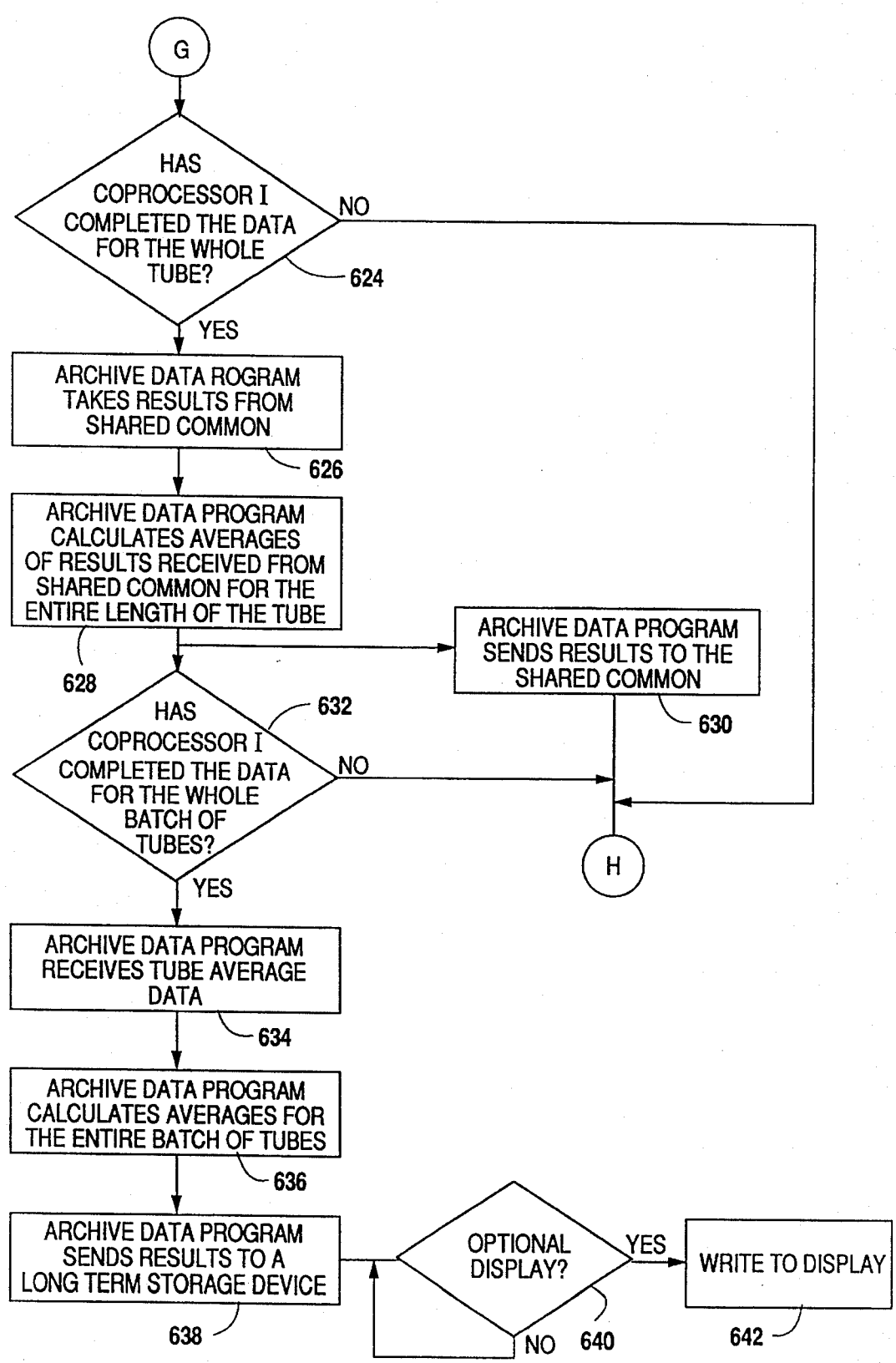

If variances in eccentricity, ovality, ID, OD or wall thickness are discovered in steps 558, 562, 566, 572 and 578 (FIGS. 8*d* and 8*e*), coprocessor III 126 calculates stepping motor 60 adjustments required to modify the manufacturing process to prevent and cure variances in steps 560, 564, 568–570, 574–576 and 580–582 respectively (FIGS. 8*d* and 8*e*). In step 584 (FIG. 8*f*), coprocessor III 126 examines the pattern of localized wall thickness variances along the length of the tube P. In step 586, if the local wall thickness variances are discovered to be periodic, in step 588 coprocessor III 126 compares the period 151 (FIG. 9*f*) of the flaw to roller ODs and IDs, and, in step 590, generates a signal indicating which rollers most likely caused the variance. If, in step 592, the variances are discovered to be continuous and longitudinal on the inner surface 154 (FIG. 9*d*) of the tube, then in step 594 coprocessor III 126 generates a signal that the plug in the plug mill 8 needs to be replaced. If, in step 596, the variance is found to be continuous and spiralling on the inner surface 161 (FIG. 9*h*) of the tube, then in step 600 coprocessor III 126 compares the spiral to the rate of rotation of the tube P in the piercer 6, elongator 7 and reeler 9 to determine which plug is causing the variance. Based on this comparison, in step 602, coprocessor III 126 generates a signal indicating which plug needs to be replaced. If, in step 604 (FIG. 8*g*), the variance is determined to be a continuous spiral 163 on the outer surface 155 (FIG. 9*h*), then in step 606 coprocessor III 126 compares the spiral defect to the diameters of the rollers and the rate of rotation of the tube P in the piercer 6, elongator 7 and reeler 9 to determine which rollers are causing the variance. Based upon this comparison, in step 608 coprocessor III 126 generates a signal indicating which rollers are most likely causing the variance. In step 610, if the variance is discovered to be continuous and longitudinal on the outer surface 155 (FIG. 9*c*) of the tube, then in step 612, coprocessor III 126 searches for a periodic aspect of the variance. If a periodic aspect is found, in step 614 coprocessor III 126 compares the period of the variance to roller OD and ID in the plug mill 8 and sizing mill 10. Based on this comparison, in step 616 coprocessor III 126 generates a signal indicating which rollers are most likely causing the variance.

In step 618, coprocessor III 126 averages the corrective signals generated for each step-up motor. In step 620, coprocessor III 126 calculates the end cut 159*e* (FIG. 9*g*) distances which were described previously. When these tasks are completed, in step 622 coprocessor III 126 makes the results available to the coprocessor III manager program 146. In step 550, the coprocessor III manager 146 places the results from coprocessor III 126 into the results partition 136 of the shared common 132. In step 623, these results are sent to the process control subsystem 50 and 54. In step 625, control signals are sent to the motor control system.

Finally, in step 603 (FIG. 8*a*), the data archive program 152 begins to perform additional tasks to the data produced by the coprocessors. In step 624 (FIG. 8*h*), if coprocessor I 122 has completed its task for a single tube P, then in step 626 the data archive program takes the coprocessor I results 136 from the shared common 132 and in step 628 calculates the average results for the entire length of the tube P. In step 630, the data archive program 152 sends the coprocessor I results 138 and the tube averages to the shared common 630. In step 632, if coprocessor I 122 has completed its task for a whole batch of tubes P, then in step 634 the data archive program 152 takes the tube average data from long term storage device 129 and in step 636 calculates averages for the entire batch of tubes P. In step 638, the data archive program 152 sends the batch averages to the long term storage device 129. All data stored in the long term storage device 129 can be accessed through the display program in order to generate production reports as shown in steps 640 and 642.

The foregoing disclosure and descriptions of the invention are illustrative and explanatory thereof, and various changes in the details of the illustrated construction may be made without departing from the spirit of the invention.

We claim:

1. A method for obtaining dimensional measurements and analyses of regularly-shaped objects during their manufacture, comprising:

a) scanning each of a plurality of cross-sections of an object with a plurality of penetrating radiation sources along a plurality of paths through each cross-section of the object;

b) generating signals representative of the radiation attenuation along each of the plurality of paths for each of the scanned cross-sections;

c) converting the attenuation signals to signals representative of the density/length of the object along each of the plurality of paths for each of the cross-sections;

d) processing the density/length signals to determine, by use of a computer model of the object to be examined, dimensional measurements for each of the cross-sections of the object scanned;

e) monitoring the position of the object as it is being scanned and generating position signals representative of the location of each of the cross-sections of the object for which dimensional measurements are being processed; and f) associating a location along the object from the generated position signals for each cross-sectional dimensional measurement; and g) creating a three-dimensional representation of the object from the plurality of cross-sectional dimensional measurements and the position signals associated therewith.

2. The method of claim 1, wherein:

a) the regularly-shaped objects comprise cylindrical objects; and b) the computer model utilizes an algorithm which presumes that the density/length signals correspond to an object with a substantially circular cross-section in order to determine the dimensional measurements of a cross-section of the object.

3. A method for obtaining nondestructive dimensional measurements of regularly-shaped objects during their manufacture, comprising:

a) scanning each of a plurality of cross-sections of an object with a plurality of penetrating radiation sources along a plurality of paths through each cross-section of the object;

b) generating signals representative of the radiation attenuation along each of the plurality of paths for each of the scanned cross-sections;

c) converting the attenuation signals to signals representative of the density/length of the object along each of the plurality of paths for each of the cross-sections;

d) processing the density/length signals to determine, by use of a computer model of the object to be examined, dimensional measurements for each of the cross-sections of the object scanned;

e) monitoring the position of the object as it is being scanned and generating position signals representative of the locations on the object of each of the cross-sections of the object for which dimensional measurements are being processed; and f) associating a location along the object from the generated position signals for each cross-sectional dimensional measurement; and g) creating a three-dimensional representation of the object from the plurality of cross-sectional measurements and the position signals associated therewith.

4. The method of claim 3, further comprising:

a) comparing the measured dimensions of the object to the dimensions of the computer model of the object to generate variance signals, wherein the resulting variance signals represent flaws;

b) accumulating variance signals associated with each scanned cross-section of the object, together with position signals associated with each scanned cross-section on the object, to generate three dimensional patterns of the flaw; and c) comparing flaw pattern characteristics to a set of known flaw pattern characteristics to determine the type of flaw.

5. The method of claim 4, wherein the step of comparing flaw pattern characteristics comprises:

comparing the accumulated flaw characteristics to a set of known flaw characteristics and their causes to diagnose the processing step causing the flaw.

6. The method of claim 5, further comprising:

a) calculating from the flaw characteristics the adjustment to the identified processing step required to cure the cause of the flaw; and b) generating a control signal in response to the adjusting calculation and transmitting it to the identified processing step to adjust the process.

7. The method of claim 6, wherein:

the identified processing step is a processing step in the manufacturing process which occurs prior to the scanning step; and the identified processing step is adjusted to prevent such detected flaws from recurring in subsequently manufactured objects.

8. The method of claim 6, wherein:

the identified processing step is a processing step in the manufacturing process which occurs after the scanning step; and the identified processing step is adjusted to cure the flaw detected in the object scanned.

9. The method of claim 6, wherein the steps of converting, processing, comparing, accumulating, calculating, measuring and determining are divided among a plurality of processors and performed in parallel.

10. The method of claim 3, further comprising:

a) measuring the temperature at each cross-section of the object as it is being scanned and generating temperature signals representative of the temperature at each cross-section of the object; and b) predicting the dimensional measurements of the scanned cross-section at a desired temperature from the temperature signal and dimensional measurements obtained at the existing temperature of the scanned cross-section using dilatometry data specific to the dimension measured.

11. The method of claim 10, further comprising:

a) comparing the measured dimensions of the object to the dimensions of the computer model of the object to generate variance signals, wherein the resulting variance signals represent flaws;

b) accumulating variance signals associated with each scanned cross-section of the object, together with position signals associated with each scanned cross-section on the object, to generate three dimensional patterns of the flaw; and c) comparing flaw pattern characteristics to set a set of known flaw pattern characteristics to determine the type of flaw.

12. The method of claim 11, wherein the step of comparing flaw pattern characteristics comprises:

comparing the accumulated flaw characteristics to a set of known flaw characteristics and their causes to diagnose the processing step causing the flaw.

13. The method of claim 12, further comprising:

a) calculating from the flaw characteristics the adjustment to the identified processing step required to cure the cause of the flaw; and b) generating a control signal in response to the adjusting calculation and transmitting it to the identified processing step to adjust the process.

14. The method of claim 13, wherein:

the identified processing step is a processing step in the manufacturing process which occurs prior to the scanning step; and the identified processing step is adjusted to prevent such detected flaws from recurring in subsequently manufactured objects.

15. The method of claim 13, wherein:

the identified processing step is a processing step in the manufacturing process which occurs after the scanning step; and the identified processing step is adjusted to cure the flaw detected in the object scanned.

16. The method of claim 13, wherein the steps of converting, processing, comparing, accumulating, calculating, measuring and determining are divided among a plurality of processors and performed in parallel.

17. The method of claim 10, wherein:

a) the regularly-shaped objects comprise cylindrical objects;

b) the computer model utilizes an algorithm which presumes that the density/length signals correspond to an object with a substantially circular cross-section in order to determine the dimensional measurements of a cross-section of the object; and c) the dilatometry data comprises a non-linear dilatometry curve.

18. A method for obtaining calibrated nondestructive dimensional measurements of regularly-shaped objects, comprising:

a) scanning an object with a plurality of penetrating radiation sources along a plurality of paths through a cross-section of the object;

b) generating signals representative of the radiation attenuation along each of the plurality of paths;

c) converting the attenuation signals to signals representative of the density/length of the object along each of the plurality of paths;

d) processing the density/length signals to determine, by use of a computer model of the object to be examined, dimensional measurements of the cross-section of the object scanned;

e) determining the thickness attenuation dependency of each of the plurality of penetrating radiation paths;

f) generating formulas representative of the thickness attenuation dependency of each penetrating radiation path; and g) adjusting the dimensional measurements using the formulas.

19. A method for obtaining nondestructive dimensional measurements of regularly-shaped objects during their manufacture, comprising:

a) scanning each of a plurality of cross-sections of an object with a plurality of penetrating radiation sources along a plurality of paths through each cross-section of the object;

b) generating digital signals representative of the radiation attenuation along each of the plurality of paths for each of the scanned cross-sections;

c) converting the attenuation signals to signals representative of the density/length of the object along each of the plurality of paths for each of the scanned cross-sections;

d) processing the density/length signals to determine, by use of a computer model of the object to be examined, dimensional measurements for each of the cross-sections of the object scanned;

e) monitoring the position of the object as it is being scanned and generating position signals representative of the location of each of the cross-sections of the object for which dimensional measurements are being processed; and f) associating a location along the object from the generated position signals for each cross-sectional dimensional measurement; and g) creating a three dimensional representation of the object from the plurality of cross-sectional measurements and the position signals associated therewith.

20. An apparatus for obtaining dimensional measurements and analyses of regularly-shaped objects during their manufacture, comprising:

a) means for scanning each of a plurality of cross-sections of an object with a plurality of penetrating radiation sources along a plurality of paths through each cross-section of the object;

b) means for generating signals representative of the radiation attenuation along each of the plurality of paths for each scanned cross-section:

c) means for converting the attenuation signals to signals representative of the density/length of the object along each of the plurality of paths for each scanned cross-section;

d) means for processing the density/length signals to determine, by use of a computer model of the object to be examined, dimensional measurements for each of the cross-sections of the object scanned;

e) means for monitoring the position of the object as it is being scanned and generating position signals representative of the location of each of the cross-sections of the object for which dimensional measurements are being processed; and f) means for associating a location along the object from the generated position signals for each cross-sectional dimensional measurement; and g) means for creating a three dimensional representation of the object from the plurality of cross-sectional measurements and the position signals associated therewith.

21. The apparatus of claim 20, wherein:

a) the regularly-shaped objects comprise cylindrical objects; and b) the computer model utilizes an algorithm which presumes that the density/length signals correspond to an object with a substantially circular cross-section in order to determine the dimensional measurements of a cross-section of the object.

22. An apparatus for obtaining nondestructive dimensional measurements of regularly-shaped objects during their manufacture, comprising:

a) means for scanning each of a plurality of cross-sections of an object with a plurality of penetrating radiation sources along a plurality of paths through each cross-section of the object;

b) means for generating signals representative of the radiation attenuation along each of the plurality of paths for each scanned cross-section;

c) means for converting the attenuation signals to signals representative of the density/length of the object along each of the plurality of paths for each scanned cross-section;

d) means for processing the density/length signals to determine, by use of a computer model of the object to be examined, dimensional measurements for each of the cross-sections of the object scanned;

e) means for monitoring the position of the object as it is being scanned and generating position signals representative of the location of each of the cross-sections of the object for which dimensional measurements are being processed; and f) means for associating a location along the object from the generated position signals for each cross-sectional dimensional measurement; and g) means for creating a three-dimensional representation of the object from the plurality of cross-sectional measurements and the position signals associated therewith.

23. The apparatus of claim 22, further comprising:

a) a computer model of the object with ideal dimensions of the object being manufactured;

b) means for comparing the measured dimensions of the object to the dimensions of the computer model of the object to generate variance signals, wherein the resulting variance signals represent flaws;

c) means for accumulating variance signals associated with each scanned cross-section of the object, together with position signals associated with each scanned cross-section on the object, to generate three dimensional patterns of the flaw;

d) a database of types of flaws and their pattern characteristics; and e) means for comparing accumulated flaw pattern characteristics to the database of flaw pattern characteristics to identify types of flaws.

24. The apparatus of claim 23, wherein the means for comparing flaw pattern characteristics comprises:
   a) a database of characteristic flaw patterns and their associated causes; and
   b) means for comparing the accumulated flaw characteristics to the database of flaw characteristics and their causes to diagnose the processing step causing the flaw.

25. The apparatus of claim 24, further comprising:
   a) means for calculating from the flaw characteristics the adjustment to the identified processing step required to cure the cause of the flaw;
   b) means to adjust the identified processing step in the manufacture of the object; and
   c) means for generating a control signal in response to the adjusting calculation and transmitting it to the adjustment means for the identified processing step to adjust the process.

26. The apparatus of claim 25, wherein:
   the identified processing step is a processing step in the manufacturing..process which occurs prior to the scanning step; and
   the identified processing step is adjusted to prevent such detected flaws from recurring in subsequently manufactured objects.

27. The apparatus of claim 25, wherein:
   the identified processing step is a processing step in the manufacturing process which occurs after the scanning step; and
   the identified processing step is adjusted to cure the flaw detected in the object scanned.

28. An apparatus for obtaining nondestructive dimensional measurements of regularly-shaped objects during their manufacture, comprising:
   a) means for scanning each of a plurality of cross-sections of an object with a plurality of penetrating radiation sources along a plurality of paths through each cross-section of the object;
   b) means for generating signals representative of the radiation attenuation along each of the plurality of paths for each scanned cross-section;
   c) means for converting the attenuation signals to signals representative of the density/length of the object along each of the plurality of paths for each scanned cross-section;
   d) means for processing the density/length signals to determine, by use of a computer model of the object to be examined, dimensional measurements for each of the cross-sections of the object scanned;
   e) means for monitoring the position of the object as it is being scanned and generating position signals representative of the location of each of the cross-sections of the object for which dimensional measurements are being processed; and
   f) means for associating a location along the object from the generated position signals for each cross-sectional dimensional measurement;
   g) means for creating a three-dimensional representation of the object from the plurality of cross-sectional measurements and the position signals associated therewith;
   h) means for measuring the temperature at each cross-section of the object as it is being scanned and generating temperature signals representative of the temperature at each cross-section of the object; and
   i) means for calculating the predicted dimensional measurements of the scanned cross-section at a desired temperature from the temperature signal and dimensional measurements obtained at the existing temperature of the scanned cross-section using dilatometry data specific to the object's shape and material composition.

29. The apparatus of claim 28, further comprising:
   a) a computer model of the object with ideal dimensions of the object being manufactured;
   b) means for comparing the measured dimensions of the object to the dimensions of the computer model of the object to generate variance signals, wherein the resulting variance signals represent flaws;
   c) means for accumulating variance signals associated with each scanned cross-section of the object, together with position signals associated with each scanned location of the cross-section on the object, to generate three dimensional patterns of the flaw;
   d) a database of types of flaws and their pattern characteristics; and
   e) means for comparing accumulated flaw pattern characteristics to the database of flaw pattern characteristics to identify types of flaws.

30. The apparatus of claim 24, wherein the means for comparing flaw pattern characteristics comprises:
   a) a database of characteristic flaw patterns and their associated causes; and
   b) means for comparing the accumulated flaw characteristics to the database of flaw characteristics and their causes to diagnose the processing step causing the flaw.

31. The apparatus of claim 30, further comprising:
   a) means for calculating from the flaw characteristics the adjustment to the identified processing step required to cure the cause of the flaw;
   b) means to adjust the identified processing steps in the manufacture of the object; and
   c) means for generating a control signal in response to the adjusting calculation and transmitting it to the adjustment means for the identified processing step to adjust the process.

32. The apparatus of claim 31, wherein
   the identified processing step is in a processing step in the manufacturing process which occurs prior to the scanning step; and
   the identified processing step is adjusted to prevent such detected flaws from recurring in subsequently manufactured objects.

33. The apparatus of claim 31, wherein
   the identified processing step is a processing step in the manufacturing process which occurs after the scanning step; and
   the identified processing step is adjusted to cure the flaw detected in the object scanned.

34. The apparatus of claim 28, wherein:
   a) the regularly-shaped objects comprise cylindrical objects;
   b) the computer model utilizes an algorithm which presumes that the density/length signals correspond to an object with a substantially circular cross-section in order to determine the dimensional measurements of a cross-section of the object; and
   c) the dilatometry data comprises a non-linear dilatometry curve.

35. An apparatus for obtaining calibrated nondestructive dimensional measurements of regularly-shaped objects, comprising:

a) means for scanning an object with a plurality of penetrating radiation sources along a plurality of paths through a cross-section of the object;
b) means for generating signals representative of the radiation attenuation along each of the plurality of paths for each cross-section;
c) means for converting the attenuation signals to signals representative of the density/length of the object along each of the plurality of paths;
d) means for processing the density/length signals to determine, by use of a computer model of the object to be examined, dimensional measurements of the cross-section of the object scanned;
e) means for determining the thickness attenuation dependency of each of the plurality of penetrating radiation paths;
f) means to generate formulas representative of the thickness attenuation dependency of the penetrating radiation paths; and
g) means to calculate the dimensional measurements using the formulas.

36. An apparatus for obtaining nondestructive dimensional measurements of regularly-shaped objects during their manufacture, comprising:
a) means for scanning each of a plurality of cross-sections of an object with a plurality of penetrating radiation sources along a plurality of paths through each cross-sections of the object;
b) means for generating digital signals representative of the radiation attenuation along each of the plurality of paths for each scanned cross-section;
c) means for converting the attenuation signals to signals representative of the density/length of the object along each of the plurality of paths for each scanned cross-section;
d) means for processing the density/length signals to determine, by use of a computer model of the object to be examined, dimensional measurements for each of the cross-sections of the object scanned;
e) means for monitoring the position of the object as it is being scanned and generating position signals representative of the location of each of the cross-sections of the object for which dimensional measurements are being processed; and
f) means for associating a location along the object from the generated position signals for each cross-sectional dimensional measurement; and
g) means for creating a three-dimensional representation of the object from the plurality of cross-sectional measurements and the position signals associated therewith.

* * * * *